(12) United States Patent
Macdonald et al.

(10) Patent No.: US 8,637,510 B2
(45) Date of Patent: Jan. 28, 2014

(54) MORPHOLINOTHIAZOLES AS ALPHA 7 POSITIVE ALLOSTERIC MODULATORS

(75) Inventors: Gregor James Macdonald, Zoersel (BE); Benoit Christian Albert Ghislain De Boeck, Genval (BE); Joseph Elisabeth Leenaerts, Rijkevorsel (BE)

(73) Assignee: Janssen Pharmaceutica NV, Beerse (BE)

( * ) Notice: Subject to any disclaimer, the term of this patent is extended or adjusted under 35 U.S.C. 154(b) by 63 days.

(21) Appl. No.: 13/512,464

(22) PCT Filed: Nov. 25, 2010

(86) PCT No.: PCT/EP2010/068193
§ 371 (c)(1),
(2), (4) Date: May 29, 2012

(87) PCT Pub. No.: WO2011/064288
PCT Pub. Date: Jun. 3, 2011

(65) Prior Publication Data
US 2012/0238561 A1    Sep. 20, 2012

(30) Foreign Application Priority Data

Nov. 27, 2009 (EP) .................................. 09177347

(51) Int. Cl.
*A61K 31/535*    (2006.01)
*C07D 413/14*    (2006.01)

(52) U.S. Cl.
USPC ....................................... 514/235.5; 544/131

(58) Field of Classification Search
USPC ....................................... 544/131; 514/235.5
See application file for complete search history.

(56) References Cited

FOREIGN PATENT DOCUMENTS

WO    WO 2009/127678 A1    10/2009

*Primary Examiner* — Rebecca Anderson
(74) *Attorney, Agent, or Firm* — Peter Herridge

(57) ABSTRACT

The present invention relates to morpholinothiazole derivatives and pharmaceutically acceptable salts thereof, processes for preparing them, pharmaceutical compositions containing them and their use in therapy. The invention particularly relates to positive allosteric modulators of nicotinic acetylcholine receptors, such positive allosteric modulators having the capability to increase the efficacy of nicotinic receptor agonists.

14 Claims, No Drawings

MORPHOLINOTHIAZOLES AS ALPHA 7 POSITIVE ALLOSTERIC MODULATORS

CROSS REFERENCE TO RELATED APPLICATIONS

This application is the national stage of PCT Application No. PCT/EP2010/068193, filed Nov. 25, 2010, which claims priority from European Patent Application No. 09177347.3, filed Nov. 27, 2009, the entire disclosures of which are hereby incorporated in their entirety.

FIELD OF THE INVENTION

The present invention relates to morpholinothiazole derivatives and pharmaceutically acceptable salts thereof, processes for preparing them, pharmaceutical compositions containing them and their use in therapy. The invention particularly relates to positive allosteric modulators of nicotinic acetylcholine receptors, such positive allosteric modulators having the capability to increase the efficacy of nicotinic receptor agonists.

BACKGROUND PRIOR ART

WO-2004/091480 discloses triazole derivatives which inhibit, regulate and/or modulate kinases, particularly Tie-2, and which may be useful to treat or prevent cancer and cancer-related disease.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called alpha subunits, and a second group containing beta subunits. Three kinds of alpha subunits, alpha 7, alpha 8 and alpha 9, have been shown to form functional receptors when expressed alone and thus are presumed to form homooligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors have been implicated in a number of diseases. Some of these, for example myasthenia gravis and autosomal dominant nocturnal front lobe epilepsy (ADNFLE) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors and since the effect of nicotine is to stabilize receptors in a desensitized state, an increased activity of nicotinic receptors may reduce the desire to smoke.

Compounds which bind nAChRs have been suggested for the treatment of a range of disorders involving reduced cholinergic function such as learning deficit, cognition deficit, attention deficit and memory loss. Modulation of alpha 7 nicotinic receptor activity is expected to be beneficial in a number of diseases including Alzheimer's disease, Lewy Body Dementia, Attention Deficit Hyperactivity Disorder, anxiety, schizophrenia, mania, bipolar disorder, Parkinson's disease, Huntington's disease, Tourette's syndrome, brain trauma and other neurological, degenerative and psychiatric disorders in which there is loss of cholinergic synapses, including jetlag, nicotine addiction, and pain.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to lose effectiveness upon chronic administration.

At nicotinic receptors in general, and of particular note at the alpha 7 nicotinic receptor, desensitization limits the duration of action of an applied agonist.

DESCRIPTION OF THE INVENTION

We have found that certain novel morpholinothiazole derivatives can increase the efficacy of agonists at nicotinic acetylcholine receptors (nAChR). Compounds having this type of action (hereinafter referred to as "positive allosteric modulators") are likely to be useful for treatment of conditions associated with reductions in nicotinic transmission. In a therapeutic setting such compounds could restore normal interneuronal communication without affecting the temporal profile of activation. In addition, positive allosteric modulators are not expected to produce long-term inactivation of receptors as may occur with prolonged application of agonists.

Positive nAChR modulators of the present invention are useful for treatment and prophylaxis of psychotic disorders, intellectual impairment disorders and diseases, inflammatory diseases and conditions in which modulation of the alpha 7 nicotinic receptor is beneficial.

The present invention concerns morpholinothiazole derivatives having positive allosteric modulator properties, in particular increasing the efficacy of agonists at the alpha 7 nicotinic receptor. The invention further relates to methods for their preparation and pharmaceutical compositions comprising them. The invention also relates to the use of these derivatives for the manufacture of a medicament for the treatment and prophylaxis of psychotic disorders, intellectual impairment disorders and diseases, inflammatory diseases and conditions in which modulation of the alpha 7 nicotinic receptor is beneficial. The invention further relates to these derivatives for use in the treatment and prophylaxis of psychotic disorders, intellectual impairment disorders and diseases, inflammatory diseases and conditions in which modulation of the alpha 7 nicotinic receptor is beneficial.

The compounds of the present invention differ structurally from the prior art compounds and do not exhibit kinase activity.

In a first aspect, the present invention relates to a compound having the formula (I)

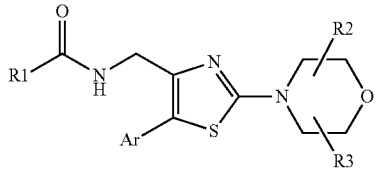

or a stereochemical isomer thereof, wherein
$R^1$ is $C_{1-6}$alkyl, $C_{3-6}$cycloalkyl, $C_{3-6}$cycloalkyl substituted with 1, 2, 3, or 4 methyl groups, $(C_{3-6}$cycloalkyl$)C_{1-6}$alkyl, $(C_{1-6}$alkyloxy$)C_{1-6}$alkyl, tetrahydrofuryl, aryl or heteroaryl;
aryl is 2,2-difluorobenzodioxanyl; phenyl; or phenyl substituted with 1, 2 or 3 substituents selected from halogen, trifluoromethyl, trifluoromethoxy, cyano, $C_{1-6}$alkyl, $C_{1-4}$alkyloxy, and aminosulfonyl;
heteroaryl is a mono- or bicyclic aromatic heterocyclic radical containing at least one heteroatom selected from N, O and S, optionally substituted with 1, 2 or where possible with 3 substituents selected from $C_{1-4}$alkyl, $C_{1-4}$alkyloxy, $C_{3-6}$cycloalkyl, or trifluoromethyl;
$R^2$ and $R^3$ are independently H or $C_{1-4}$alkyl;
Ar is

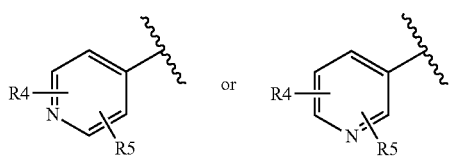

$R^4$ and $R^5$ are independently H, $C_{1-4}$alkyl, $C_{3-6}$cycloalkyl or $C_{1-4}$alkyloxy;
or an acid addition salt thereof, or a solvate thereof.

In one example, $R^1$ is $C_{1-4}$alkyl, $C_{3-6}$cycloalkyl, cyclopropyl substituted with 1, 2, 3, or 4 methyl groups, $(C_{3-6}$cycloalkyl$)C_{1-2}$alkyl, or methoxymethyl;
aryl is phenyl substituted with 1, 2, or 3 substituents selected from fluoro, chloro, methyl, methoxy, trifluoromethyl, trifluoromethoxy, cyano, and aminosulfonyl;
heteroaryl is furanyl, oxazolyl, isoxazolyl, oxadiazolyl, pyrrolyl, pyrazolyl, imidazolyl, pyridinyl, pyridiminyl, pyrazinyl, pyridazinyl or benzisoxazolyl, each unsubstituted or substituted with 1, 2 or where possible 3 substituents selected from methyl, ethyl, propyl, isopropyl, butyl, isobutyl, tert.butyl, cyclopropyl, methoxy or trifluoromethyl.

In another example $R^2$ is hydrogen or methyl.
In another example, $R^3$ is methyl.
In another example, $R^4$ is hydrogen, methyl, cyclopropyl or methoxy.
In another example, $R^5$ is hydrogen or methyl.
In another example, $R^1$ is methyl, ethyl, n-propyl, isopropyl, n-butyl, isobutyl, tert.-butyl, cyclopropyl, 1-methylcyclopropyl, 2,2,3,3-tetramethylpropyl, cyclobutyl, cyclopentyl, (cyclopropyl)ethyl, (cyclopropyl)methyl, (cyclobutyl)methyl;
Het is 3-methyl-isoxazol-5-yl, 3-methyl-isoxazol-4-yl, 5-methyl-isoxazol-3-yl, 2-methyl-5-trifluoromethyl-oxazol-4-yl, 2-methyl-oxazol-4-yl.
In another example, $R^2$ and $R^3$ are methyl and have the cis-configuration.

In another example $R^4$ is hydrogen, methyl, cyclopropyl or methoxy.
In another example, $R^5$ is methyl.
Particular compounds are
N-[[2-[(2R,6S)-2,6-dimethyl-4-morpholinyl]-5-(2,6-dimethyl-4-pyridinyl)-4-thiazolyl]methyl]-cyclopropaneacetamide;
N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide;
N-[[2-[(2R,6S)-2,6-dimethyl-4-morpholinyl]-5-(2,6-dimethyl-4-pyridinyl)-4-thiazolyl]methyl]-3-methyl-5-isoxazolecarboxamide; and
N-[[2-[(2R,6S)-2,6-dimethyl-4-morpholinyl]-5-(2,6-dimethyl-4-pyridinyl)-4-thiazolyl]methyl]-acetamide.

In a second aspect, the present invention relates to a compound having the formula (I)

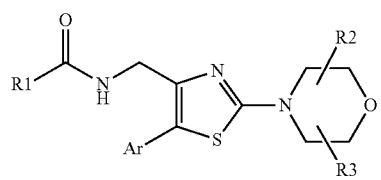

or a stereochemical isomer thereof, wherein
$R^1$ is $C_{1-6}$alkyl, $C_{1-6}$alkyl substituted with 1, 2 or 3 halogen substituents, $C_{1-6}$alkyl substituted with 1 cyano group, $C_{1-6}$alkyl substituted with 1 heteroaryl group, $C_{3-6}$cycloalkyl, $C_{3-6}$cycloalkyl substituted with 1, 2, 3, or 4 methyl groups, $C_{3-6}$cycloalkyl substituted with 1 hydroxy group, $(C_{3-6}$cycloalkyl$)C_{1-6}$alkyl, $(C_{1-6}$alkyloxy$)C_{1-6}$alkyl, (halo$C_{1-4}$alkyloxy$)C_{1-6}$alkyl, tetrahydrofuryl, aryl, heteroaryl, pyrrolidinyl, pyrrolidinyl substituted with 1 $C_{1-4}$alkyl group, or tetrahydrofuryl substituted with 1, 2 or 3 substituents selected from methyl and oxo;
aryl is 2,2-difluoro-1,3-benzodioxolyl; phenyl; or phenyl substituted with 1, 2 or 3 substituents selected from halogen, trifluoromethyl, trifluoromethoxy, cyano, $C_{1-6}$alkyl, $C_{1-4}$alkyloxy, and aminosulfonyl;
heteroaryl is a mono- or bicyclic aromatic heterocyclic radical containing at least one heteroatom selected from N, O and S, optionally substituted with 1, 2 or where possible with 3 substituents selected from $C_{1-4}$alkyl, $C_{1-4}$alkyloxy, $C_{3-6}$cycloalkyl, and trifluoromethyl;
$R^2$ and $R^3$ are independently H, $C_{1-4}$alkyl or trifluoromethyl; or $R^2$ and $R^3$ are taken together to form 1,2-ethanediyl or 1,3-propanediyl;
Ar is

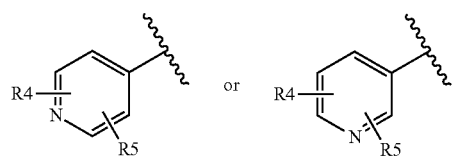

$R^4$ and $R^5$ are independently H, $C_{1-4}$alkyl, trifluoromethyl, $C_{3-6}$cycloalkyl or $C_{1-4}$alkyloxy;
or an acid addition salt thereof, or a solvate thereof.

In one example, $R^1$ is $C_{1-4}$alkyl, $C_{3-6}$cycloalkyl, cyclopropyl substituted with 1, 2, 3, or 4 methyl groups, $(C_{3-6}$cycloalkyl$)C_{1-2}$alkyl, or methoxymethyl;

aryl is phenyl substituted with 1, 2, or 3 substituents selected from fluoro, chloro, methyl, methoxy, trifluoromethyl, trifluoromethoxy, cyano, and aminosulfonyl;
heteroaryl is furanyl, oxazolyl, isoxazolyl, oxadiazolyl, pyrrolyl, pyrazolyl, imidazolyl, pyridinyl, pyridiminyl, pyrazinyl, pyridazinyl or benzisoxazolyl, each unsubstituted or substituted with 1, 2 or where possible 3 substituents selected from methyl, ethyl, propyl, isopropyl, butyl, isobutyl, tert.butyl, cyclopropyl, methoxy, and trifluoromethyl.

In another example,
$R^1$ is $C_{1-6}$alkyl, $C_{1-4}$alkyl substituted with 3 fluoro substituents, methyl substituted with 1 cyano group, methyl substituted with 3,5-dimethyl-4-ixoxazolyl, methyl substituted with 3-methyl-5-isoxazolyl, $C_{3-6}$cycloalkyl, cyclopropyl substituted with 1, 2, 3, or 4 methyl groups, cyclopropyl substituted with 1 hydroxy group,
($C_{3-6}$cycloalkyl)$C_{1-2}$alkyl, methoxymethyl, methoxyethyl, (2,2,2-trifluoroethoxy)methyl, tetrahydrofuryl, aryl, heteroaryl, pyrrolidinyl substituted with 1 methyl group, or tetrahydrofuryl substituted with 3 substituents selected from methyl and oxo;
aryl is 2,2-difluoro-1,3-benzodioxol-5-yl; 2,2-difluoro-1,3-benzodioxol-4-yl; phenyl; or phenyl substituted with 1, 2 or 3 substituents selected from fluoro, chloro, trifluoromethyl, trifluoromethoxy, cyano, methyl, methoxy, and aminosulfonyl; in particular aryl is phenyl substituted with 1, 2 or 3 substituents selected from fluoro, chloro, trifluoromethyl, trifluoromethoxy, cyano, methyl, methoxy, and aminosulfonyl;
heteroaryl is furanyl, oxazolyl, isoxazolyl, oxadiazolyl, pyrrolyl, pyrazolyl, imidazolyl, pyridinyl, pyridiminyl, pyrazinyl, pyridazinyl, thienyl, 1,2,3-thiadiazolyl, thiazolyl or benzisoxazolyl, each unsubstituted or substituted with 1, 2 or where possible 3 substituents selected from methyl, ethyl, propyl, isopropyl, butyl, isobutyl, tert.butyl, cyclopropyl, methoxy and trifluoromethyl; in particular heteroaryl is furanyl, oxazolyl, isoxazolyl, pyrazolyl, pyridinyl, pyrazinyl, thienyl, 1,2,3-thiadiazolyl, thiazolyl or benzisoxazolyl, each unsubstituted or substituted with 1, 2 or where possible 3 substituents selected from methyl, isopropyl, tert.butyl, cyclopropyl, methoxy and trifluoromethyl.

In another example,
$R^1$ is $C_{1-6}$alkyl, $C_{1-4}$alkyl substituted with 3 fluoro substituents, methyl substituted with 1 cyano group, methyl substituted with 3,5-dimethyl-4-ixoxazolyl, methyl substituted with 3-methyl-5-isoxazolyl, $C_{3-6}$cycloalkyl, cyclopropyl substituted with 1, 2, 3, or 4 methyl groups, cyclopropyl substituted with 1 hydroxy group, ($C_{3-6}$cycloalkyl)$C_{1-2}$alkyl, methoxymethyl, methoxyethyl, (2,2,2-trifluoroethoxy)methyl, tetrahydrofuryl, aryl, heteroaryl, pyrrolidinyl substituted with 1 methyl group, or tetrahydrofuryl substituted with 3 substituents selected from methyl and oxo;
aryl is 2,2-difluoro-1,3-benzodioxol-5-yl; 2,2-difluoro-1,3-benzodioxol-4-yl; phenyl; or phenyl substituted with 1, 2 or 3 substituents selected from fluoro, chloro, trifluoromethyl, trifluoromethoxy, cyano, methyl, methoxy, and aminosulfonyl; in particular aryl is phenyl substituted with 1, 2 or 3 substituents selected from fluoro, chloro, trifluoromethyl, trifluoromethoxy, cyano, methyl, methoxy, and aminosulfonyl;
heteroaryl is furanyl, oxazolyl, isoxazolyl, oxadiazolyl, pyrrolyl, pyrazolyl, imidazolyl, pyridinyl, pyridiminyl, pyrazinyl, pyridazinyl, thienyl, 1,2,3-thiadiazolyl, thiazolyl or benzisoxazolyl, each unsubstituted or substituted with 1, 2 or where possible 3 substituents selected from methyl, ethyl, propyl, isopropyl, butyl, isobutyl, tert.butyl, cyclopropyl, methoxy and trifluoromethyl; in particular heteroaryl is furanyl, oxazolyl, isoxazolyl, pyrazolyl, pyridinyl, pyrazinyl, thienyl, 1,2,3-thiadiazolyl, thiazolyl or benzisoxazolyl, each unsubstituted or substituted with 1, 2 or where possible 3 substituents selected from methyl, isopropyl, tert.butyl, cyclopropyl, methoxy and trifluoromethyl;
$R^2$ and $R^3$ are independently H, methyl or trifluoromethyl;
or $R^2$ and $R^3$ are taken together to form 1,2-ethanediyl;
Ar is

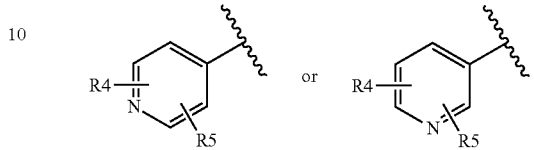

$R^4$ and $R^5$ are independently H, methyl, trifluoromethyl, cyclopropyl or methoxy.

In another example $R^2$ is hydrogen or methyl.

In another example, $R^3$ is methyl.

In another example, $R^4$ is hydrogen, methyl, cyclopropyl or methoxy.

In another example, $R^5$ is hydrogen or methyl.

In another example, $R^1$ is methyl, ethyl, n-propyl, isopropyl, n-butyl, isobutyl, tert.butyl, cyclopropyl, 1-methylcyclopropyl, 2,2,3,3-tetramethylpropyl, cyclobutyl, cyclopentyl, (cyclopropyl)ethyl, (cyclopropyl)methyl, (cyclobutyl)methyl;
Het is 3-methyl-isoxazol-5-yl, 3-methyl-isoxazol-4-yl, 5-methyl-isoxazol-3-yl, 2-methyl-5-trifluoromethyl-oxazol-4-yl, 2-methyl-oxazol-4-yl.

In another example, $R^1$ is methyl, ethyl, n-propyl, isopropyl, n-butyl, isobutyl, tert.butyl, cyclopropyl, 1-methylcyclopropyl, 2,2,3,3-tetramethylcyclopropyl, cyclobutyl, cyclopentyl, (cyclopropyl)ethyl, (cyclopropyl)methyl, (cyclobutyl)methyl;
Het is 3-methyl-isoxazol-5-yl, 3-methyl-isoxazol-4-yl, 5-methyl-isoxazol-3-yl, 2-methyl-5-trifluoromethyl-oxazol-4-yl, 2-methyl-oxazol-4-yl.

In another example, $R^1$ is cyclopropyl or 3-methyl-4-isoxazolyl; in particular 3-methyl-4-isoxazolyl.

In another example, $R^1$ is $C_{1-6}$alkyl, $C_{1-6}$alkyl substituted with 1, 2 or 3 halogen substituents, $C_{1-6}$alkyl substituted with 1 cyano group, $C_{1-6}$alkyl substituted with 1 heteroaryl group, $C_{3-6}$cycloalkyl, $C_{3-6}$cycloalkyl substituted with 1, 2, 3, or 4 methyl groups, $C_{3-6}$cycloalkyl substituted with 1 hydroxy group, ($C_{3-6}$cycloalkyl)$C_{1-6}$alkyl, ($C_{1-6}$alkyloxy)$C_{1-6}$alkyl, (halo$C_{1-4}$alkyloxy)$C_{1-6}$alkyl, tetrahydrofuryl, aryl, heteroaryl, pyrrolidinyl, pyrrolidinyl substituted with 1 $C_{1-4}$alkyl group,
or tetrahydrofuryl substituted with 1 oxo group and 1 or 2 methyl groups.

In another example, $R^2$ and $R^3$ are methyl and have the cis-configuration.

In another example, $R^2$ and $R^3$ are methyl and have the trans-configuration.

In another example, $R^2$ and $R^3$ are independently H, $C_{1-4}$alkyl or trifluoromethyl; in particular $R^2$ and $R^3$ are independently H, methyl or trifluoromethyl.

In another example, $R^2$ and $R^3$ are independently H, $C_{1-4}$alkyl or trifluoromethyl;
or $R^2$ and $R^3$ are taken together to from 1,2-ethanediyl;
in particular $R^2$ and $R^3$ are independently H, methyl or trifluoromethyl;
or $R^2$ and $R^3$ are taken together to from 1,2-ethanediyl.

In another example, $R^4$ and $R^5$ are independently H, methyl, trifluoromethyl, cyclopropyl or methoxy.

In another example, R² and R³ are independently H, methyl or trifluoromethyl; and R⁴ and R⁵ are independently H, methyl, trifluoromethyl, cyclopropyl or methoxy.

In another example, R² and R³ are independently H, methyl or trifluoromethyl;
or R² and R³ are taken together to from 1,2-ethanediyl;
and R⁴ and R⁵ are independently H, methyl, trifluoromethyl, cyclopropyl or methoxy.

In another example, R⁴ is H, methyl, trifluoromethyl, cyclopropyl or methoxy; in particular H, methyl, cyclopropyl or methoxy.

In another example, R⁵ is methyl.
In another example, R⁴ and R⁵ are methyl.
In another example, Ar is

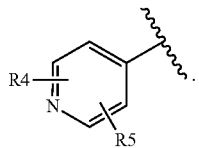

In another example, Ar is

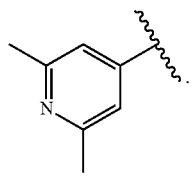 [SMILES: *c1cc(C)nc(C)c1]

In another example heteroaryl is furanyl, oxazolyl, isoxazolyl, oxadiazolyl, pyrrolyl, pyrazolyl, imidazolyl, pyridinyl, pyridiminyl, pyrazinyl, pyridazinyl, thienyl, 1,2,3-thiadiazolyl, thiazolyl or benzisoxazolyl, each unsubstituted or substituted with 1, 2 or where possible 3 substituents selected from methyl, ethyl, propyl, isopropyl, butyl, isobutyl, tert.butyl, cyclopropyl, methoxy and trifluoromethyl; more in particular heteroaryl is furanyl, oxazolyl, isoxazolyl, pyrazolyl, pyridinyl, pyrazinyl, thienyl, 1,2,3-thiadiazolyl, thiazolyl or benzisoxazolyl, each unsubstituted or substituted with 1, 2 or where possible 3 substituents selected from methyl, isopropyl, tert.butyl, cyclopropyl, methoxy and trifluoromethyl;

In another example
R¹ is cyclopropyl or 3-methyl-4-isoxazolyl; in particular 3-methyl-4-isoxazolyl;
R² and R³ are methyl and have the cis configuration;
Ar is

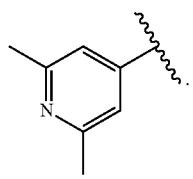 [SMILES: *c1cc(C)nc(C)c1]

Particular compounds are
N-[[2-[(2R,6S)-2,6-dimethyl-4-morpholinyl]-5-(2,6-dimethyl-4-pyridinyl)-4-thiazolyl]methyl]-cyclopropaneacetamide;
N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide;
N-[[2-[(2R,6S)-2,6-dimethyl-4-morpholinyl]-5-(2,6-dimethyl-4-pyridinyl)-4-thiazolyl]methyl]-3-methyl-5-isoxazolecarboxamide; and
N-[[2-[(2R,6S)-2,6-dimethyl-4-morpholinyl]-5-(2,6-dimethyl-4-pyridinyl)-4-thiazolyl]methyl]-acetamide;
including any stereochemical isomer form thereof, and the acid addition salts and the solvates thereof.

Particular compounds are
N-[[2-[(2R,6S)-2,6-dimethyl-4-morpholinyl]-5-(2,6-dimethyl-4-pyridinyl)-4-thiazolyl]methyl]-cyclopropaneacetamide;
N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide;
N-[[2-[(2R,6S)-2,6-dimethyl-4-morpholinyl]-5-(2,6-dimethyl-4-pyridinyl)-4-thiazolyl]methyl]-3-methyl-5-isoxazolecarboxamide; and
N-[[2-[(2R,6S)-2,6-dimethyl-4-morpholinyl]-5-(2,6-dimethyl-4-pyridinyl)-4-thiazolyl]methyl]-acetamide.

Particular compounds are
N-[[2-[(2R,6S)-2,6-dimethyl-4-morpholinyl]-5-(2,6-dimethyl-4-pyridinyl)-4-thiazolyl]methyl]-cyclopropaneacetamide; and
N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide.

A particular compound is
N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide; including any stereochemical isomer form thereof, and the acid addition salts and the solvates thereof.

A particular compound is
N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide.

All possible combinations of the above-indicated interesting embodiments are considered to be embraced within the scope of this invention.

When describing the compounds of the invention, the terms used are to be construed in accordance with the following definitions, unless a context dictates otherwise.

The term "halo" or "halogen" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms.

Alkyl groups may be linear or branched and may be substituted as indicated herein. When a subscript is used herein following a carbon atom, the subscript refers to the number of carbon atoms that the named group may contain.

Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-6}$alkyloxy" as a group or part of a group refers to a radical having the Formula —OR$^a$ wherein R$^a$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula —OR$^b$ wherein R$^b$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "halo$C_{1-4}$alkyloxy" as a group or part of a group refers to a $C_{1-4}$alkyloxy radical wherein said $C_{1-4}$alkyloxy radical is further substituted with 1, 2 or 3 halo atoms. Non-limiting examples of suitable halo$C_{1-4}$alkyloxy radicals include trifluoromethyloxy, trifluoroethyloxy, trifluoropropyloxy, and trifluorobutyloxy.

The term "$C_{3-6}$cycloalkyl" alone or in combination, refers to a cyclic saturated hydrocarbon radical having from 3 to 6 carbon atoms. Non-limiting examples of suitable cyclo$C_{3-6}$alkyl include cyclopropyl, cyclobutyl, cyclopentyl and cyclohexyl.

It will be appreciated that some of the compounds according to formula (I) and the addition salts, hydrates and solvates thereof may contain one or more centers of chirality and exist as stereoisomeric forms.

The term "stereoisomeric forms" as used hereinbefore or hereinafter defines all the possible stereoisomeric forms which the compounds according to formula (I) and their addition salts may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their salts, solvates, substantially free, i.e. associated with less than 10%, preferably less than 5%, in particular less than 2% and most preferably less than 1% of the other isomers.

For therapeutic use, salts of the compounds according to formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds according to formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The term solvates refers to hydrates and alcoholates which the compounds according to formula (I) as well as the salts thereof, may form.

The chemical names of the compounds of the present invention were generated according to the nomenclature rules agreed upon by the Chemical Abstracts Service, using Advanced Chemical Development, Inc., nomenclature software (ACD/Name product version 10.01; Build 15494, 1 Dec. 2006).

Some of the compounds according to formula (I) may also exist in their tautomeric form. Such forms although not explicitly indicated in the above formula are intended to be included within the scope of the present invention.

Preparation of the Compounds

Compounds of Formula (I) can be prepared by reacting a compound of Formula (II),

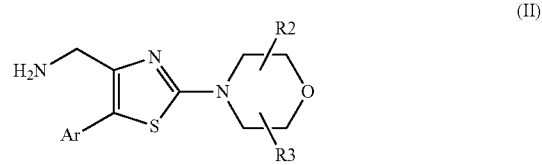

where Ar, R$^1$ and R$^2$ are as defined in Formula (I), with a compound of Formula (III)

where R$^1$ is as defined in Formula (I), in the presence of a suitable amide coupling reagent, such as HBTU, a suitable base, such as DIPEA, in a suitable solvent, such as DCM and at a suitable temperature, such as room temperature. Alternatively, the acylation reaction of (II) may be conducted with a symmetric or asymmetric anhydride, or an acyl halide of carboxylic acid (III).

Compounds of Formula (II), can be prepared by reacting a compound of Formula (IV),

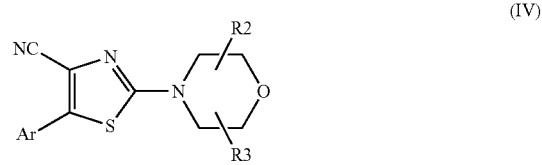

where Ar, R$^2$ and R$^3$ are as defined in Formula (I), with a suitable reducing agent, such as hydrogen, in the presence of a suitable catalyst, such as Raney Nickel, in a suitable solvent, such as 7M ammonia in methanol, at a suitable temperature, such as room temperature.

Compounds of Formula (IV) can be prepared by reacting a compound of Formula (V)

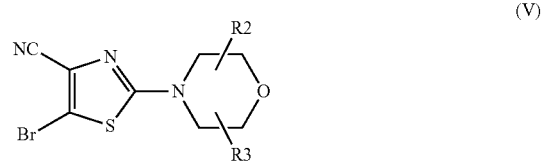

where, $R^2$ and $R^3$ are as defined in Formula (I), with a compound of Formula (VI)

$$Ar\!-\!B(OH)_2 \qquad (VI)$$

where Ar is as defined in Formula (I), in the presence of a suitable catalyst, such as $Pd(PPh_3)_4$, with a suitable base, such as sodium carbonate, in a suitable solvent, such as 1,4-dioxane and ethanol/water (1:1) and at a suitable temperature, such as 130° C. in a sealed tube.

Compounds of Formula (V) can be prepared by reacting a compound of Formula (VII)

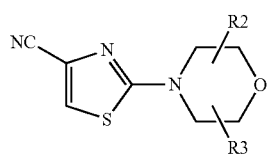

(VII)

where $R^2$ and $R^3$ are as defined in Formula (I), with N-bromosuccinimide, in a suitable solvent, such as DMF and at a suitable temperature, such as room temperature.

Compounds of Formula (VII) can be prepared by reacting a compound of Formula (VIII)

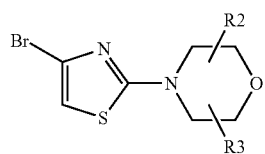

(VIII)

where $R^2$ and $R^3$ are as defined in Formula (I) with zinc cyanide, in the presence of suitable catalysts, such as a mixture of 10% Pd on Carbon, triphenylphosphine and trimethylsilyl chloride, or a mixture of tetrakis(triphenylphosphine) palladium and triphenylphosphine, in a suitable solvent, such as DMF or acetonitrile and at a suitable temperature, such as 80° C.

Compounds of Formula (VIII) can be prepared by reacting a compound of Formula (IX)

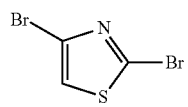

(IX)

with a compound of Formula (X)

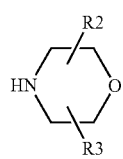

(X)

where $R^2$ and $R^3$ are as defined in Formula (I), in the presence of a suitable base, such as DIPEA, in a suitable solvent, such as DMF, at a suitable temperature, such as 75° C. and under a suitable inert atmosphere, such a argon.

Pharmacology

The compounds of the present invention were found to be positive allosteric modulators of the alpha 7 nicotinic receptor. The alpha 7 nicotinic receptor (alpha 7 nAChR) belongs to the superfamily of cys-loop, ionotropic ligand-gated ion channels which includes the $5\text{-}HT_3$, $GABA_A$ and glycine receptor families. It is activated by acetylcholine and its breakdown product choline and a major feature of the alpha 7 nAChR is its rapid desensitisation in the persistent presence of agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans. It is also implicated in the cholinergic inflammatory pathway.

Genetic evidence for its association with schizophrenia is seen in the form of strong linkage between a schizophrenia marker (sensory gating deficit) and the alpha 7 locus on 15q13-14 and polymorphisms in the core promoter region of the alpha 7 gene.

Pathological evidence points to a loss of alpha 7 immunoreactivity and α-bungarotoxin (Btx)-binding in the hippocampus, frontal and cingulate cortex of schizophrenic brains, in Parkinson's and Alzheimer's disease, and in the paraventricular nucleus and nucleus reuniens in autism.

Pharmacological evidence such as the marked smoking habits of schizophrenics compared to normals has been interpreted as an attempt by the patients to self-medicate to make up for a deficit in alpha 7 nicotinergic transmission. Transient normalization of defects in sensory gating (pre-pulse inhibition, PPI) in both animal models and man upon nicotine administration and temporary restoration of normal sensory gating in schizophrenics when forebrain cholinergic activity is low (e.g. stage 2 sleep) have both been interpreted to be the result of transient activation of the alpha 7 nicotinic receptor followed by desensitization.

Thus there is good reason to suppose that activating the alpha 7 nAChR will have therapeutically beneficial effects for a number of CNS (psychiatric and neurological) disorders.

As already mentioned the alpha 7 nAChR rapidly desensitizes in the persistent presence of the natural transmitter acetylcholine as well as exogenous ligands such as nicotine. In the desensitized state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatible and desensitized alpha 7 nAChRs in a physiologically useful range. However, synthetic agonists, which are not substrates for the natural breakdown and clearance mechanisms are perceived to have a potential liability both for over-stimulation and also to push the alpha 7 nAChR population equilibrium towards a persistently desensitized state, which is undesirable in disorders in which deficiencies in alpha 7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to alpha 7 agonism is to enhance receptor responsiveness to the natural agonists with a positive allosteric modulator (PAM). A PAM is defined as an agent which binds to a site distinct from the agonist binding site, and therefore is not expected to have agonist or desensitization properties, but enhances the responsiveness of the alpha 7 nAChR to the natural transmitter. The value of this strategy is that for a given amount of transmitter the magnitude of the alpha 7 nAChR response is increased in the presence of the PAM relative to the level of transmission possible in its absence. Additionally, PAMs can also increase the potency of the natural transmitter. So for disorders in which there is a deficit in alpha 7 nAChR protein, the PAM-induced increase in alpha 7 nicotinergic transmission can be beneficial. As a PAM relies on the presence of the natural transmitter the potential for over-stimulation is limited by the breakdown/clearance mechanisms for the natural transmitter.

The compounds of the present invention are classified as type 1-4, based on qualitative kinetic properties, as determined by whole-cell voltage-clamp recordings. This classification is based on the effect of an alpha 7 PAM compound, as described hereinbefore, on the signal elicited by an agonist application. In particular, said agonist is choline at a concentration of 1 mM. In a preferred experimental setting, said alpha 7 PAM compound and choline are simultaneously applied to the cell, as described hereinafter. Desensitization is defined as the closure of the receptor upon activation during the application of the agonist in whole-cell voltage-clamp electrophysiology measurements seen as the reduction of the outward current after initial activation by the agonist.

The definition of the PAM types 1-4 is described hereinafter:

Type 0 compounds minimally change the effect size of the current elicited by 1 mM choline.

Type 1 compounds enhance the effect size of the current elicited by 1 mM choline but minimally alter the kinetics of the receptor. In particular, the rate and the extent of desensitization and of deactivation of the receptor elicited by the agonist is not affected. The compound-modulated response to 1 mM choline, therefore, is close to a linear scaling of the 1 mM choline response in absence of the alpha 7 PAM compound.

Type 2 compounds enhance the effect size of the current elicited by 1 mM choline while reducing the rate and/or the extent of desensitization. Deactivation of the receptor is generally unaffected.

Type 3 compounds enhance the effect size of the current elicited by 1 mM choline. When tested at higher concentrations up to 10 µM they completely inhibit desensitization, in particular a 1 mM choline application of 250 milliseconds. Deactivation of the receptor may be slowed down Type 4 compounds allow for an initial desensitization of the receptor followed by a re-opening of the receptor during agonist application. At low-potency concentrations of the alpha 7 PAM compound, the agonist-induced activation, which is followed by desensitization, can still be separated from the compound-induced re-opening as an initial inward current-maximum. At higher potency concentrations of the alpha 7 PAM compound, the re-opening occurs faster than the closure due to desensitization so that the initial current-maximum disappears.

A compound was considered to have interesting PAM-like activity when the potentiation of the peak current was at least 200% compared to the control choline response (=100%). Such compounds are classified as belonging to a particular PAM type in the Experimental Part. Compounds not meeting the condition are not classified as belonging to a particular PAM-type.

A number of compounds according to the invention have proven active in the auditory evoked potential test. The DBA/2 inbred mouse strain used in this test shows sensory processing deficits similar to schizophrenia patients which are also correlated with reduced nicotinic alpha 7 receptors in the hippocampus. The DBA/2 mouse has proven to be a useful model of schizophrenia-like sensory processing deficits. Human studies of nicotine effects on sensory processing predicted the results in the DBA/2 mouse and studies with the selective alpha 7 agonist GTS-21 in DBA/2 mice, predicted the effects in humans. This model of sensory gating ability therefore has high translational relevance.

It is accordingly an object of the present invention to provide methods of treatment that include administering either a positive allosteric modulator as the only active substance, thus modulating the activity of endogenous nicotinic receptor agonists such as acetylcholine or choline, or administering a positive allosteric modulator together with a nicotinic receptor agonist. In a particular form of this aspect of the invention, the method of treatment comprises treatment with a positive allosteric modulator of the alpha 7 nicotinic receptor as described herein and an alpha 7 nicotinic receptor agonist or partial agonist. Examples of suitable compounds with alpha 7 nicotinic receptor agonistic activity include 1,4-Diazabicyclo[3.2.2]nonane-4-carboxylic acid, 4-bromophenyl ester, monohydrochloride (SSR180711A);
(−)-spiro[1-azabicyclo[2.2.2.]octane-3,5'-oxazolidine]-2'-one;
3-[(2,4-Dimethoxy)Benzylidene]-Anabaseine Dihydrochloride (GTS-21);
[N-[(3R)-1-Azabicyclo[2.2.2]oct-3-yl]-4-chlorobenzamide Hydrochloride] PNU-282987;
nicotine;
varenicline;
MEM3454;
AZD-0328;
MEM63908;
(+)-N-(1-azabicyclo[2.2.2]oct-3-yl)benzo[b]furan-2-carboxamide;
A-582941;
AR-R17779;
TC-1698;
PHA-709829;
tropisetron;
WAY-317538;
EVP-6124; and
TC-5619.

In particular, examples of suitable compounds with α7 nicotinic receptor agonistic activity include 1,4-Diazabicyclo [3.2.2]nonane-4-carboxylic acid, 4-bromophenyl ester, monohydrochloride (SSR180711A);
(−)-spiro[1-azabicyclo[2.2.2.]octane-3,5'-oxazolidine]-2'-one;
3-[(2,4-Dimethoxy)Benzylidene]-Anabaseine Dihydrochloride (GTS-21);
[N-[(3R)-1-Azabicyclo[2.2.2]oct-3-yl]-4-chlorobenzamide Hydrochloride] PNU-282987; nicotine; varenicline; MEM3454; AZD-0328; and MEM63908.

Positive nAChR modulators of the present invention are useful for treatment or prophylaxis of psychotic disorders, intellectual impairment disorders or diseases or conditions in which modulation of alpha 7 nicotinic receptor activity is beneficial. A particular aspect of the method of the invention is a method of treatment for learning deficit, cognition deficit, attention deficit or memory loss, modulation of alpha 7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

The compounds may also find therapeutical use as anti-inflammatory medicines because the nicotinic acetylcholine receptor alpha 7 subunit is essential for inhibiting cytokine synthesis by the cholinergic inflammatory pathway. Examples of indications which may be treated by the compounds are endotoxaemia, endotoxic shock, sepsis, rheumatoid arthritis, asthma, multiple sclerosis, psoriasis, urticaria, inflammatory bowel disease, inflammatory bile disease, Crohn's disease, ulcerative colitis, post-operative ileus, pancreatitis, heart failure, acute lung injury and allograft rejection.

The compounds of the invention may find therapeutical use in the following indications as cognition in schizophrenia, cognition in Alzheimer's disease, mild cognitive impairment, Parkinson's disease, attention deficit hyperactivity disorder, ulcerative colitis, pancreatitis, arthritis, sepsis, postoperative ileus and acute lung injury.

Compound 22 was profiled for kinase activity in an assay comprising more than 225 different kinases; the compound did not show activity against any of the tested kinases.

In view of the above described pharmacological properties, the compounds according to formula (I) or any subgroup thereof, their pharmaceutically acceptable addition salts, solvates and stereochemically isomeric forms, may be used as a medicine. In particular, the present compounds can be used for the manufacture of a medicament for treatment or prophylaxis of psychotic disorders, intellectual impairment disorders or diseases or conditions in which modulation of the alpha 7 nicotinic receptor is beneficial.

In an embodiment the present invention relates to the compounds according to formula (I) for use in the treatment or prophylaxis, in particular treatment of psychotic disorders, intellectual impairment disorders or diseases or conditions in which modulation of the α7 nicotinic receptor is beneficial.

In an embodiment the present invention relates to the compounds according to formula (I) for use in the treatment or prophylaxis, in particular treatment, of psychotic disorders, intellectual impairment disorders, or inflammatory diseases.

In an embodiment the present invention relates to the compounds according to formula (I) for treating or preventing, in particular treating, said diseases or conditions.

In view of the utility of the compounds according to formula (I), there is provided a method of treating or preventing warm-blooded animals, including humans, suffering from diseases in which modulation of the alpha 7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said methods comprise the administration, i.e. the systemic or topical administration, preferably oral administration, of an effective amount of a compound according to formula (I), a stereochemically isomeric form thereof, a pharmaceutically acceptable addition salt, or a solvate thereof, to warm-blooded animals, including humans.

One skilled in the art will recognize that a therapeutically effective amount of the PAM's of the present invention is the amount sufficient to modulate the activity of the alpha 7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the alpha 7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 µM, and more usually 5 nM to 50 µM. To obtain these treatment concentrations, a patient in need of treatment likely will be administered between 0.01 mg/kg to 2.50 mg/kg body weight, in particular from 0.1 mg/kg to 0.50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Pharmaceutical Compositions

The present invention also provides compositions for preventing or treating diseases in which modulation of the alpha 7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds according to formula (I) may also be used in combination with other conventional alpha 7 nicotinic receptor agonists, such as for example
1,4-Diazabicyclo[3.2.2]nonane-4-carboxylic acid, 4-bromophenyl ester, monohydrochloride (SSR180711A);
(−)-spiro[1-azabicyclo[2.2.2.]octane-3,5'-oxazolidine]-2'-one;
3-[(2,4-dimethoxy)benzylidene]-anabaseine dihydrochloride (GTS-21);
[N-[(3R)-1-Azabicyclo[2.2.2]oct-3-yl]-4-chlorobenzamide Hydrochloride] PNU-282987; nicotine; varenicline; MEM3454; AZD-0328 and MEM63908.

The compounds according to formula (I) may also be used in combination with other conventional α7 nicotinic receptor agonists, such as for example
1,4-Diazabicyclo[3.2.2]nonane-4-carboxylic acid, 4-bromophenyl ester, monohydrochloride (SSR180711A);
(−)-spiro[1-azabicyclo[2.2.2.]octane-3,5'-oxazolidine]-2'-one;

3-[(2,4-Dimethoxy)Benzylidene]-Anabaseine Dihydrochloride (GTS-21); [N-[(3R)-1-Azabicyclo[2.2.2]oct-3-yl]-4-chlorobenzamide Hydrochloride] PNU-282987; nicotine; varenicline; MEM3454; AZD-0328; MEM63908; (+)-N-(1-azabicyclo [2.2.2]oct-3-yl)benzo[b]furan-2-carboxamide; A-582941; AR-R17779; TC-1698; PHA-709829; tropisetron; WAY-317538; EVP-6124; and TC-5619.

Thus, the present invention also relates to the combination of a compound according to formula (I) and a alpha 7 nicotinic receptor agonist. Said combination may be used as a medicine. The present invention also relates to a product comprising (a) a compound according to formula (I), and (b) an alpha 7 nicotinic receptor agonist, as a combined preparation for simultaneous, separate or sequential use in the treatment of diseases wherein modulation of the alpha 7 nicotinic receptor is beneficial. The different drugs may be combined in a single preparation together with pharmaceutically acceptable carriers.

EXPERIMENTAL PART

Several methods for preparing the compounds of this invention are illustrated in the following Examples. Unless otherwise noted, all starting materials were obtained from commercial suppliers and used without further purification.

Hereinafter or hereinbefore, "DMF" means N,N-dimethylformamide; "min" means minutes; "MeOH" means methanol; "EtOH" means ethanol; "Et$_2$O" means diethyl ether; "TFA" means trifluoroacetic acid; "iPrNH$_2$" means isopropylamine; "NH$_4$OAc" means ammonium acetate; "SFC" means supercritical fluid chromatography; "HBTU" means O-(benzotriazol-1-yl)-N,N,N',N'-tetramethyluronium hexafluorophosphate; "DIPEA" means diisopropylethylamine; "DCM" means dichloromethane; "DIPE" means diisopropylether.

Microwave assisted reactions were performed in a single-mode reactor: Initiator™ Sixty EXP microwave reactor (Biotage AB), or in a multimode reactor: MicroSYNTH Labstation (Milestone, Inc.).

The absolute stereochemical configuration for some of the compounds was determined using vibrational circular dichroism (VCD). A description on the use of VCD for the determination of absolute configuration can be found in Dyatkin A. B. et. al, *Chirality*, 14:215-219 (2002).

The following examples are intended to illustrate but not to limit the scope of the present invention.

A. Preparation of the Intermediates 4-(4-Bromo-thiazol-2-yl)-cis-2,6-dimethyl-morpholine (Intermediate 1)

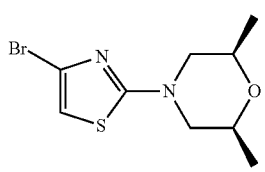
(Intermediate 1)

A 1 L flask equipped with a mechanical stirrer and a thermometer was charged with 2,4-dibromothiazole (60 g, 0.247 mol) and DMF (480 mL). After dissolution, cis-2,6-dimethylmorpholine (33.65 mL, 0.272 mol) and DIPEA (61.23 mL, 0.37 mol) were added under a stream of nitrogen. The reaction mixture was heated to 70° C. under nitrogen and stirred overnight. The reaction mixture was cooled to 10° C. in an ice/water bath. Then water (1 L) was added dropwise in a temperature range of 10-20° C. A slightly exothermic reaction was observed, with formation of an off-white precipitate. After the addition, the reaction mixture was stirred for 30 min. The precipitate was then filtered and washed with water (50 ml). The collected solid was dried in a vacuum oven at 50° C., yielding 52.8 g (77%) of Intermediate 1 as an off-white solid.

2-(cis-2,6-dimethyl-morpholin-4-yl)-thiazole-4-carbonitrile (Intermediate 2)

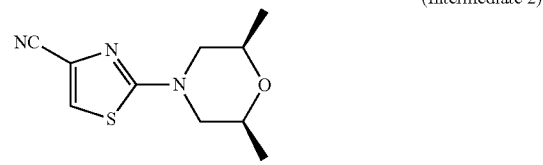
(Intermediate 2)

A mixture of Intermediate 1 (52.8 g, 190.49 mmol), triphenylphosphine (4.99 g, 19.05 mmol), zinc cyanide (22.37 g, 190.49 mmol) and dry acetonitrile (360 mL) was introduced in a pressure tube and was degassed with nitrogen for 5 min. Tetrakis(triphenylphosphine)palladium (11 g, 9.52 mmol) was added and the mixture was further degassed for 5 min. The tube was sealed and the reaction mixture was stirred at 140° C. for 3 h. The suspension was evaporated and taken up in water/DCM. The combined organic layer was separated, filtered on a plug of diatomaceous earth, dried on MgSO4, filtered off, and evaporated. The residue was purified on an 800 g EasyVarioPrep (Merck) column (eluent: DCM). The desired fractions were concentrated in vacuo and dried in a vacuum oven at 50° C. overnight, yielding 25.6 g (60%) of Intermediate 2 as a yellow solid.

5-Bromo-2-(cis-2,6-dimethyl-morpholin-4-yl)-thiazole-4-carbonitrile (Intermediate 3)

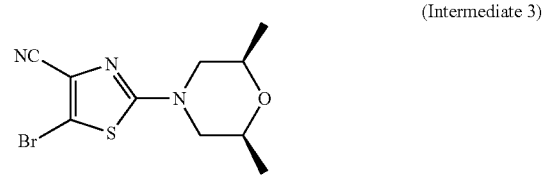 [SMILES: C[C@@H]1CN(c2nc(C#N)c(Br)s2)C[C@H](C)O1]
(Intermediate 3)

A flask charged with Intermediate 2 (25.61 g, 114.69 mmol) and DMF (250 mL) was cooled in an ice/water bath. N-bromosuccinimide (24.49 g, 137.63 mmol) was added portionwise (slightly exothermic reaction). The reaction mixture was stirred at room temperature for 10 min. Water (400 mL) was then added dropwise leading to a yellow precipitate, followed by sodium hydroxide 1 M (115 mL). The precipitate was filtered, washed with water (50 mL) and DIPE (10 mL).

This solid was recrystallised from acetonitrile. Filtration and overnight drying in a vacuum oven at 50° C. yielded 25.5 g (73%) of Intermediate 3 as a yellow solid.

2-(cis-2,6-dimethyl-morpholin-4-yl)-5-(2,6-dimethyl-pyridin-4-yl)-thiazole-4-carbonitrile (Intermediate 4)

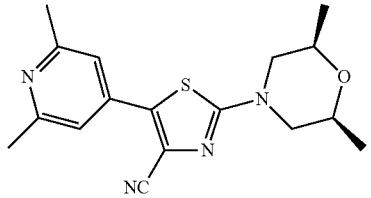
(Intermediate 4)

A mixture of Intermediate 3 (20 g, 66.18 mmol), 2,6-dimethylpyridine-4-boronic acid, pinacol ester ([325142-95-8], 20 g, 85.79 mmol), tetrakis(triphenylphosphine)palladium (4.59 g, 3.97 mmol), 1,4-dioxane (120 mL), sodium carbonate (21.04 g, 198.55 mmol) in ethanol/water 1/1 (120 mL) was stirred and heated under nitrogen atmosphere at 130° C. for 6 h. The solvent was evaporated. The residue was taken up in DCM and washed twice with water. The organic layer was separated, dried with MgSO$_4$ and evaporated. The residue was purified by column chromatography on silica gel (eluent gradient from 100% DCM to 98/2 DCM/MeOH). The desired fractions were collected and evaporated. The resulting residue was recrystallized from DIPE/CH$_3$CN, yielding 18.5 g (85%) of Intermediate 4, after drying overnight under vacuum at 50° C.

[2-(cis-2,6-dimethyl-morpholin-4-yl)-5-(2,6-dimethyl-pyridin-4-yl)-thiazol-4-yl]-methylamine (Intermediate 5)

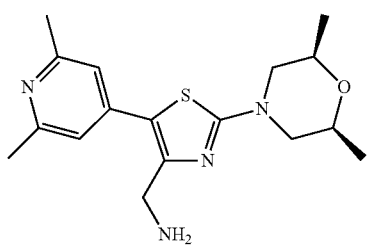
(Intermediate 5)

Intermediate 4 (18.5 g, 56.33 mmol) was added to a suspension of Raney Nickel (2 g) in a 7 N ammonia solution in MeOH (250 mL). The reaction mixture was stirred at 14° C. under hydrogen atmosphere until 2 equivalents of hydrogen were absorbed. The catalyst was removed by filtration over diatomaceous earth. The solvent was evaporated, yielding Intermediate 5 quantitatively. Intermediate 5 was used without further purification.

2-Methoxy-6-methyl-pyridine-4-boronic acid (Intermediate 6)

(Intermediate 6)

A mixture of 2-methoxy-6-methylpyridine (4.9 g, 39.79 mmol), bis(pinacolato)diboron ([73183-34-3], 10.1 g, 39.79 mmol) and 4,4-di-tert-butyl-2,2-dipyridyl ([72914-19-3], 64 mg, 0.24 mmol) in dry octane (75 mL) was stirred at room temperature while nitrogen was bubbled through the mixture during 15 min. Bis(1,5-cyclooctadiene)diiridium(I) dichloride ([12112-67-3], 80 mg, 0.12 mmol) was added and the reaction mixture was brought to reflux and refluxed for 4 h. The reaction mixture was cooled, diluted with DCM (100 mL) and transferred to a beaker equiped with a magnetic stirrer. Water (125 mL) was added portionwise while stirring (gas evolution) and the mixture was vigorously stirred for 15 min. The organic layer was separated and the water layer was extracted 3 times with DCM. The combined organic layers were dried over MgSO$_4$, filtered and concentrated. The residue was purified by column chromatography on silica gel with an eluent gradient from 100% DCM to 95/5 DCM/MeOH, yielding the corresponding boronate ester ([1083168-87-9]). After a few weeks of standing at room temperature, this ester was converted completely to Intermediate 6 (3.5 g, 52%) that was used without further purification.

2,5-Dimethylpyridine-4-boronic acid, pinacol ester (Intermediate 7)

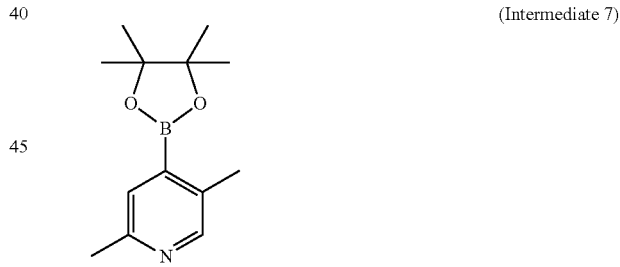
(Intermediate 7)

A mixture of 2,5-lutidine (5 g, 46.66 mmol), bis(pinacolato)diboron ([73183-34-3], 11.85 g, 46.66 mmol) and 4,4-di-tert-butyl-2,2-dipyridyl ([72914-19-3], 50 mg, 0.19 mmol) in dry octane (50 mL) was stirred at room temperature while nitrogen was bubbled through the mixture during 10 min. Bis(1,5-cyclooctadiene)diiridium(I) dichloride ([12112-67-3], 63 mg, 0.09 mmol) was added and the reaction mixture was brought to reflux and refluxed overnight. The reaction mixture was cooled, diluted with DCM (600 mL) and transferred to a beker equiped with a magnetic stirrer. Ice-cold water (400 mL) was added carefully while stirring (gas evolution) and the mixture was vigorously stirred for 15 min. The mixture was filtered on diatomaceous earth. The organic layer was separated and the water layer was extracted twice with DCM. The combined organic layers were washed with water, dried over MgSO$_4$, filtered and concentrated, yielding 2.1 g (17%) of Intermediate 7 that was used without further purification.

2-Cyclopropyl-6-methylpyridine-4-boronic acid, pinacol ester (Intermediate 8)

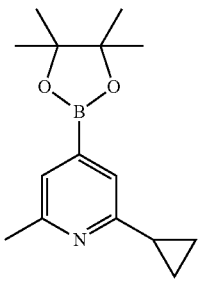

(Intermediate 8)

A mixture of 2-cyclopropyl-6-methylpyridine ([41765-00-8], 1.1 g, 8.26 mmol), bis(pinacolato)diboron ([73183-34-3], 2.09 g, 8.26 mmol) and 4,4-di-tert-butyl-2,2-dipyridyl ([72914-19-3], 9 mg, 0.03 mmol) in dry octane (20 mL) was stirred at room temperature while nitrogen was bubbled through the mixture during 15 min. Bis(1,5-cyclooctadiene)diiridium(I) dichloride ([12112-67-3], 11 mg, 0.02 mmol) was added and the reaction mixture was brought to reflux and refluxed overnight. The reaction mixture was cooled, diluted with DCM (50 mL) and transferred to a beker equiped with a magnetic stirrer. Water (50 mL) was added portionwise while stirring (gas evolution) and the mixture was vigorously stirred for 15 min. The organic layer was separated and the water layer was extracted 3 times with DCM. The combined organic layers were dried over MgSO$_4$, filtered and concentrated, yielding Intermediate 8 (2.01 g, 91%) that was used without further purification.

Cis-2-trifluoromethyl-6-methylmorpholine (Intermediate 29)

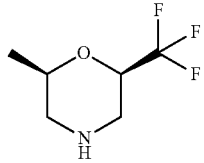

(Intermediate 29)

N-benzyl-cis-2-trifluoromethyl-6-methylmorpholine [679839-97-5] (6.2 g, 23.91 mmol) was added to a suspension of Pd/C 10% (1 g) in methanol (150 mL). The reaction mixture was stirred at room temperature under a hydrogen atmosphere until 1 equivalent of hydrogen was absorbed. The catalyst was removed by filtration over diatomaceous earth. The solvent was evaporated, yielding 3.1 g (77%) of Intermediate 29 as an oil that was used without further purification.

Trans-2-trifluoromethyl-6-methylmorpholine (Intermediate 30)

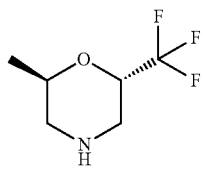

(Intermediate 30)

N-benzyl-trans-2-trifluoromethyl-6-methylmorpholine [1223452-62-7] (7.5 g, 28.93 mmol) was added to a suspension of Pd/C 10% (1 g) in methanol (150 mL). The reaction mixture was stirred at room temperature under a hydrogen atmosphere until 1 equivalent of hydrogen was absorbed. The catalyst was removed by filtration over diatomaceous earth. The solvent was evaporated, yielding 3.3 g (67%) of Intermediate 30 as an oil that was used without further purification.

TABLE 1

The following intermediates were prepared according to the procedures used for Intermediate 5 (starting from Intermediate 3, via Intermediate 4):

| Intermediate | Structure | Starting from |
|---|---|---|
| 9 | 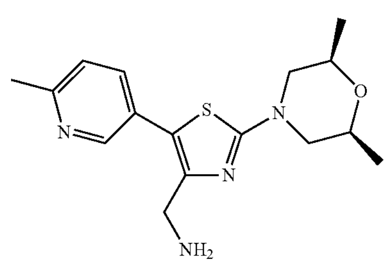 | Intermediate 3 and 2-picoline-5-boronic acid hydrate ([1072952-30-7]) |

TABLE 1-continued

The following intermediates were prepared according to the procedures used for
Intermediate 5 (starting from Intermediate 3, via Intermediate 4):

| Intermediate | Structure | Starting from |
|---|---|---|
| 10 | 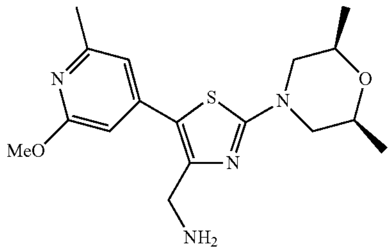 [SMILES: COc1cc(-c2sc(N3C[C@@H](C)O[C@@H](C)C3)nc2CN)cc(C)n1] | Intermediate 3 and Intermediate 6 |
| 11 | 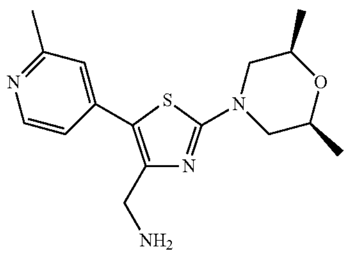 [SMILES: Cc1cc(-c2sc(N3C[C@@H](C)O[C@@H](C)C3)nc2CN)ccn1] | Intermediate 3 and 2-methylpyridine-4-boronic acid, pinacol ester ([660867-80-1]) |
| 12 | 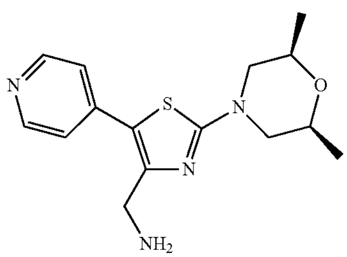 [SMILES: C[C@@H]1CN(c2nc(CN)c(-c3ccncc3)s2)C[C@H](C)O1] | Intermediate 3 and pyridine-4-boronic acid ([1692-15-5]) |
| 13 | 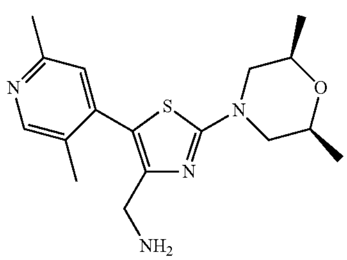 [SMILES: Cc1cc(-c2sc(N3C[C@@H](C)O[C@@H](C)C3)nc2CN)c(C)cn1] | Intermediate 3 and Intermediate 7 |
| 14 | 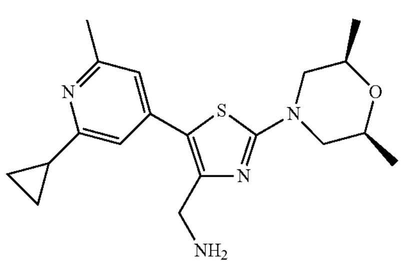 [SMILES: Cc1cc(-c2sc(N3C[C@@H](C)O[C@@H](C)C3)nc2CN)cc(C2CC2)n1] | Intermediate 3 and Intermediate 8 |

TABLE 1-continued

The following intermediates were prepared according to the procedures used for
Intermediate 5 (starting from Intermediate 3, via Intermediate 4):

| Intermediate | Structure | Starting from |
|---|---|---|
| 22 | 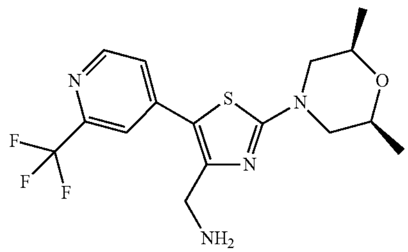 [SMILES: C[C@@H]1CN(c2nc(CN)c(-c3ccnc(C(F)(F)F)c3)s2)C[C@H](C)O1] | Intermediate 3 and 2-trifluoromethylpyridine-4-boronic acid [1093407-58-9] |

TABLE 2

The following intermediates were prepared according to the procedures used for
Intermediate 5 (starting from 2,4-dibromothiazole, via Intermediates 1, 2, 3, and 4):

| Intermediate | Structure | Starting from |
|---|---|---|
| 15 | 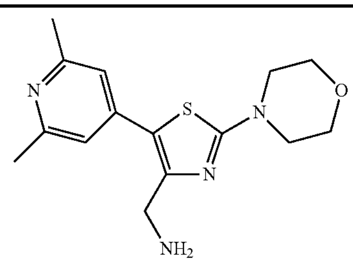 | 2,4-dibromothiazole and morpholine |
| 16 | Trans | 2,4-dibromothiazole and cis/trans 2,6-dimethylmorpholine, separating the trans isomer from the cis in the first step by column chromatography on silica gel (eluent: heptanes/DCM 50/50 to 0/100) |
| 17 | 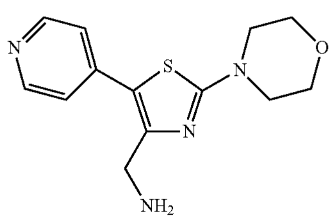 [SMILES: NCc1nc(N2CCOCC2)sc1-c1ccncc1] | 2,4-dibromothiazole and morpholine, and using pyridine-4-boronic acid ([1692-15-5]) instead of 2,6-dimethylpyridine-4-boronic acid, pinacol ester |
| 23 | 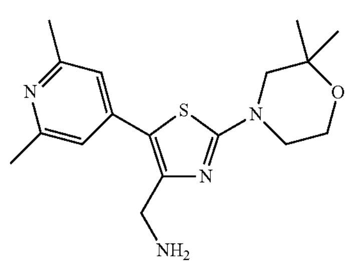 | 2,4-dibromothiazole and 2,2-dimethylmorpholine |

TABLE 2-continued

The following intermediates were prepared according to the procedures used for Intermediate 5 (starting from 2,4-dibromothiazole, via Intermediates 1, 2, 3, and 4):

| Intermediate | Structure | Starting from |
|---|---|---|
| 24 | 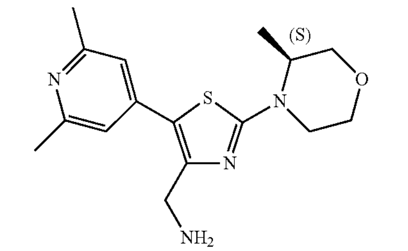 | 2,4-dibromothiazole and 3-(S)-methylmorpholine |
| 25 | 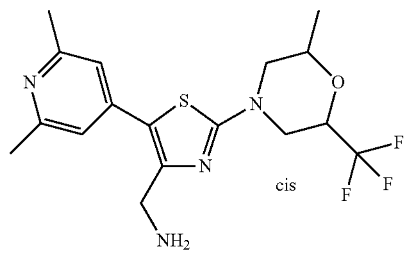 [SMILES: Cc1cc(-c2sc(N3CC(C)OC(C(F)(F)F)C3)nc2CN)cc(C)n1] | 2,4-dibromothiazole and Intermediate 29 |
| 26 | 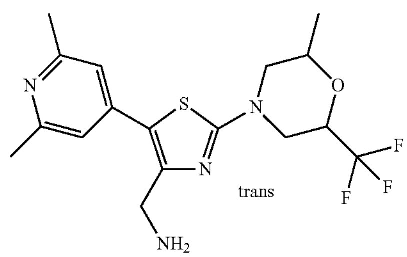 [SMILES: Cc1cc(-c2sc(N3CC(C)OC(C(F)(F)F)C3)nc2CN)cc(C)n1] | 2,4-dibromothiazole and Intermediate 30 |
| 27 | 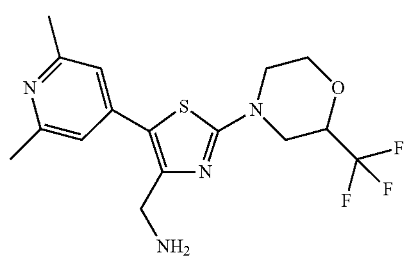 [SMILES: Cc1cc(-c2sc(N3CCOC(C(F)(F)F)C3)nc2CN)cc(C)n1] | 2,4-dibromothiazole and 2-trifluoromethylmorpholine |
| 28 | 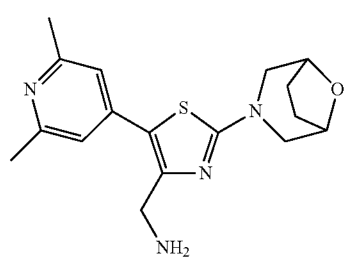 [SMILES: Cc1cc(-c2sc(N3CC4CCC(C3)O4)nc2CN)cc(C)n1] | 2,4-dibromothiazole and 8-oxa-3-azabicyclo[3.2.1]octane hydrochloride |

(Intermediates 18 (*R) and 19 (*S))

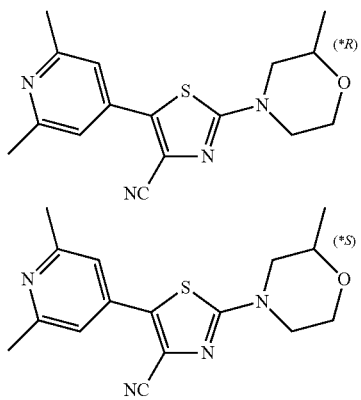

Intermediates 18 (*R) and 19 (*S) were prepared according to the procedure used for Intermediate 4, starting from 2-methylmorpholine instead of 2,6-dimethylmorpholine. The two enantiomers were separated by preparative supercritical fluid chromatography (SFC) on a Chiralpak Diacel AD 30×250 mm column, using 81% CO₂, 19% MeOH with 0.2% iPrNH₂ as mobile phase.

(Intermediates 20 (*R) and 21 (*S))

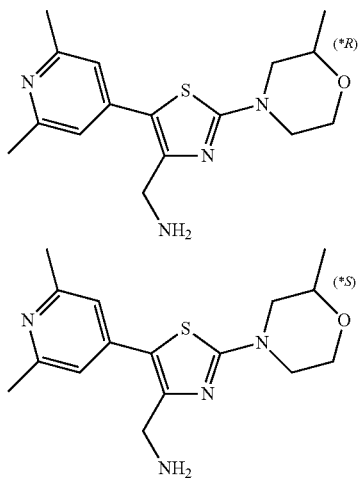

Intermediates 20 (*R) and 21 (*S) were prepared according to the procedure used for Intermediate 5, starting from Intermediates 18 and 19, respectively.

B. Preparation of the Final Compounds

B1) Example 1

N-[[2-[(2R,6S)-2,6-dimethyl-4-morpholinyl]-5-(2,6-dimethyl-4-pyridinyl)-4-thiazolyl]methyl]-cyclopropaneacetamide (Compound 1)

(Compound 1)

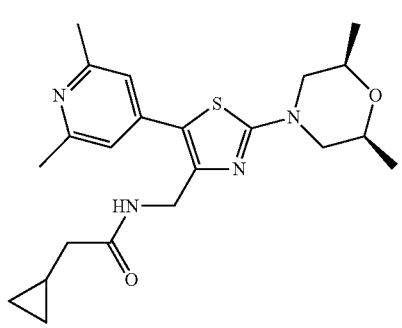

A mixture of cyclopropylacetic acid (5 g, 49.94 mmol), HBTU (19.16 g, 50.53 mmol) and DIPEA (15.31 mL, 92.64 mmol) in 250 ml dichloromethane was stirred for 15 min at room temperature. Intermediate 5 (14 g, 42.11 mmol) in 80 ml dichloromethane was added dropwise and stirring was continued for 2 hours at room temperature.

The reaction mixture was treated with 1N NaOH and the organic layer was washed three times with water. The organic layer was separated, dried with MgSO₄ and concentrated under reduced pressure.

This residue was purified on a silica column with an eluent gradient from 100% DCM to 98/2 DCM/MeOH. The corresponding pure fractions were collected and evaporated. The product was treated with Et2O, filtered and dried in vacuum, yielding 11.8 g (68%) of Compound 1.

B2) Example 2

N-[[2-[(2R,6S)-2,6-dimethyl-4-morpholinyl]-5-(2,6-dimethyl-4-pyridinyl)-4-thiazolyl]methyl]-3-methyl-5-isoxazolecarboxamide (Compound 4)

(Compound 4)

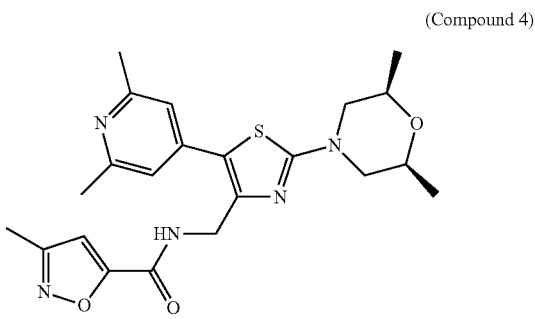

DIPEA (0.16 mL, 0.97 mmol) was added to a solution of Intermediate 5 (150 mg, 0.45 mmol) in DCM (6 mL). The reaction mixture was cooled to 0° C. under nitrogen atmosphere. 3-Methylisoxazole-5-carbonyl chloride (79 mg, 0.54 mmol) was then added dropwise and stirring was continued for 1 h at room temperature. The reaction was washed with sodium bicarbonate and then twice with water. The organic layer was dried over a magnesium sulphate plug and evaporated. The residue was purified by preparative HPLC (RP Shandon Hyperprep C18 BDS—8 μm, 250 g, 5 cm; mobile phase (0.25% NH₄HCO₃ solution in water, CH₃CN)), yielding 127 mg (64%) of Compound 4.

B3) Example 3

N-[[2-[(2R,6S)-2,6-dimethyl-4-morpholinyl]-5-(2,6-dimethyl-4-pyridinyl)-4-thiazolyl]methyl]-acetamide (Compound 60)

(Compound 60)

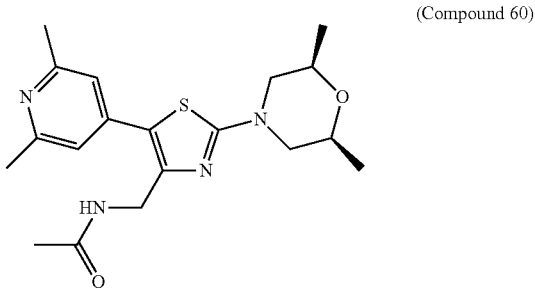

A mixture of Intermediate 5 (150 mg, 0.45 mmol) and triethylamine (0.063 mL, 0.54 mmol) was stirred in dichloromethane (6 mL) at room temperature. Acetic acid anhydride (0.051 mL, 0.54 mmol) was added and the reaction mixture was stirred at room temperature for 2 h. The reaction mixture was washed with a potassium carbonate solution. The organic layer was dried on MgSO$_4$, filtered, and evaporated. The residue was purified by preparative HPLC (RP Shandon Hyperprep C18 BDS—8 μm, 250 g, 5 cm; mobile phase (0.25% NH$_4$HCO$_3$ solution in water, MeOH+ CH$_3$CN)), yielding 100 mg (59%) of Compound 60.

B4) Example 4

N-[[5-(2,6-dimethyl-4-pyridinyl)-2-[(2R,6R)-2-methyl-6-(trifluoromethyl)-4-morpholinyl]-4-thiazolyl]methyl]-cyclopropaneacetamide (Compound 203) and N-[[5-(2,6-dimethyl-4-pyridinyl)-2-[(2S,6S)-2-methyl-6-(trifluoromethyl)-4-morpholinyl]-4-thiazolyl]methyl]-cyclopropaneacetamide (Compound 204)

(Compound 203 (2R, 6R) and Compound 204 (2S, 6S))

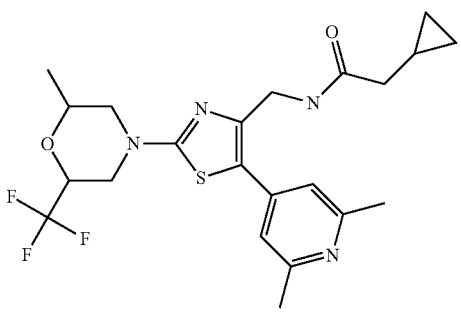

Compound 202 (obtained via an analogous procedure as described in B1) was purified into its enantiomers by preparative SFC (on Chiralpak® Daicel AD 30×250 mm, coupled with AD 20×250 mm; mobile phase: CO$_2$, EtOH with 0.2% iPrNH$_2$). The two product fractions were collected and the solvent was evaporated in both cases. The residues were dissolved in MeOH and the solvent was evaporated again in both cases. Compound 203 was pure after these steps, Compound 204 still contained an amount of the other isomer, thus the compound was re-purified following the same method, to obtain pure Compound 204.

B5) Example 5

N-[[5-(2,6-dimethyl-4-pyridinyl)-2-[2-methyl-6-(trifluoromethyl)-4-morpholinyl]-4-thiazolyl]methyl]-cyclopropaneacetamide (trans A enantiomer) (Compound 206) N-[[5-(2,6-dimethyl-4-pyridinyl)-2-[2-methyl-6-(trifluoromethyl)-4-morpholinyl]-4-thiazolyl]methyl]-cyclopropaneacetamide (trans B enantiomer) (Compound 133)

(Compound 206 (trans A) and Compound 133 (trans B))

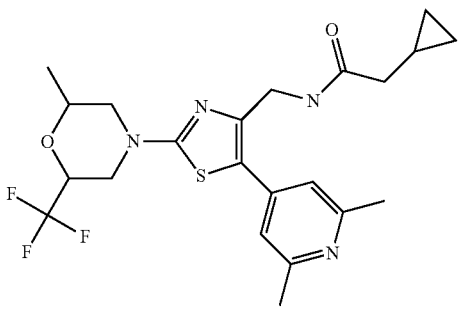

Compound 205 (obtained via an analogous procedure as described in B1) was purified into its enantiomers by preparative SFC (on Chiralpak® Daicel AD 30×250 mm, coupled with AD 20×250 mm; mobile phase: CO$_2$, MeOH with 0.2% iPrNH$_2$). The two product fractions were collected and the solvent was evaporated in both cases. The residues were dissolved in MeOH and the solvent was evaporated again in both cases, yielding Compound 206 and Compound 133.

B6) Example 6

N-[[5-(2,6-dimethyl-4-pyridinyl)-2-[(2R)-2-(trifluoromethyl)-4-morpholinyl]-4-thiazolyl]methyl]-cyclopropaneacetamide (Compound 191) N-[[5-(2,6-dimethyl-4-pyridinyl)-2-[(2S)-2-(trifluoromethyl)-4-morpholinyl]-4-thiazolyl]methyl]-cyclopropaneacetamide (Compound 192)

(Compound 191 (2R) and Compound 192 (2S))

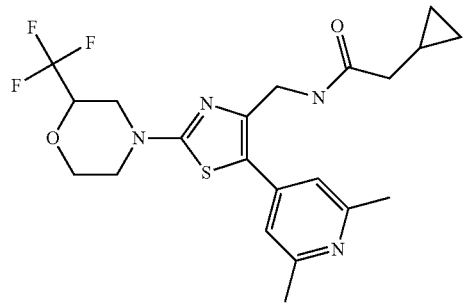

Compound 190 (obtained via an analogous procedure as described in B1) was purified into its enantiomers by preparative SFC (on Chiralpak® Daicel AD 20×250 mm; mobile phase: CO$_2$, MeOH with 0.2% iPrNH$_2$). The two product fractions were collected and the solvent was evaporated in both cases. The residues were dissolved in MeOH and the solvent was evaporated again in both cases, yielding Compound 191 (white powder). Compound 192 was still not pure and was purified again by preparative SFC (on Chiralpak® Daicel AD 20×250 mm; mobile phase: CO$_2$, MeOH with 0.2% iPrNH$_2$). The desired fractions were collected and the solvent was evaporated. This residue was dissolved in MeOH and evaporated again, yielding Compound 192 (white powder).

TABLE 3

Final compounds

| Co. No. | Chemical Name | R1 | Exp. No. |
|---|---|---|---|
| 1 | N-[[2-[(2R,6S)-2,6-dimethyl-4-morpholinyl]-5-(2,6-dimethyl-4-pyridinyl)-4-thiazolyl]methyl]-cyclopropaneacetamide | cyclopropyl-CH2- | B1 |
| 2 | N-[[2-[(2R,6S)-2,6-dimethyl-4-morpholinyl]-5-(2,6-dimethyl-4-pyridinyl)-4-thiazolyl]methyl]-cyclobutanecarboxamide | cyclobutyl- | B2 |
| 3 | N-[[2-[(2R,6S)-2,6-dimethyl-4-morpholinyl]-5-(2,6-dimethyl-4-pyridinyl)-4-thiazolyl]methyl]-5-methyl-3-isoxazolecarboxamide | 5-methyl-isoxazol-3-yl | B1 |
| 4 | N-[[2-[(2R,6S)-2,6-dimethyl-4-morpholinyl]-5-(2,6-dimethyl-4-pyridinyl)-4-thiazolyl]methyl]-3-methyl-5-isoxazolecarboxamide | 3-methyl-isoxazol-5-yl | B2 |
| 5 | 2-chloro-N-[[2-[(2R,6S)-2,6-dimethyl-4-morpholinyl]-5-(2,6-dimethyl-4-pyridinyl)-4-thiazolyl]methyl]-benzamide | 2-chlorophenyl | B2 |
| 6 | N-[[2-[(2R,6S)-2,6-dimethyl-4-morpholinyl]-5-(2,6-dimethyl-4-pyridinyl)-4-thiazolyl]methyl]-2-fluoro-benzamide | 2-fluorophenyl | B2 |
| 7 | N-[[2-[(2R,6S)-2,6-dimethyl-4-morpholinyl]-5-(2,6-dimethyl-4-pyridinyl)-4-thiazolyl]methyl]-3-fluoro-benzamide | 3-fluorophenyl | B2 |
| 8 | N-[[2-[(2R,6S)-2,6-dimethyl-4-morpholinyl]-5-(2,6-dimethyl-4-pyridinyl)-4-thiazolyl]methyl]-4-fluoro-benzamide | 4-fluorophenyl | B2 |
| 9 | 3-chloro-N-[[2-[(2R,6S)-2,6-dimethyl-4-morpholinyl]-5-(2,6-dimethyl-4-pyridinyl)-4-thiazolyl]methyl]-benzamide | 3-chlorophenyl | B2 |

TABLE 3-continued

Final compounds

| Co. No. | Chemical Name | R1 | Exp. No. |
|---|---|---|---|
| 10 | 2,4-dichloro-N-[[2-[(2R,6S)-2,6-dimethyl-4-morpholinyl]-5-(2,6-dimethyl-4-pyridinyl)-4-thiazolyl]methyl]-benzamide | 2,4-dichlorophenyl | B2 |
| 11 | N-[[2-[(2R,6S)-2,6-dimethyl-4-morpholinyl]-5-(2,6-dimethyl-4-pyridinyl)-4-thiazolyl]methyl]-4-(trifluoromethoxy)-benzamide | 4-(trifluoromethoxy)phenyl | B2 |
| 12 | 3-cyano-N-[[2-[(2R,6S)-2,6-dimethyl-4-morpholinyl]-5-(2,6-dimethyl-4-pyridinyl)-4-thiazolyl]methyl]-benzamide | 3-cyanophenyl | B2 |
| 13 | N-[[2-[(2R,6S)-2,6-dimethyl-4-morpholinyl]-5-(2,6-dimethyl-4-pyridinyl)-4-thiazolyl]methyl]-2,4-difluoro-benzamide | 2,4-difluorophenyl | B2 |
| 14 | N-[[2-[(2R,6S)-2,6-dimethyl-4-morpholinyl]-5-(2,6-dimethyl-4-pyridinyl)-4-thiazolyl]methyl]-2,3,4-trifluoro-benzamide | 2,3,4-trifluorophenyl | B2 |
| 15 | N-[[2-[(2R,6S)-2,6-dimethyl-4-morpholinyl]-5-(2,6-dimethyl-4-pyridinyl)-4-thiazolyl]methyl]-3,5-difluoro-benzamide | 3,5-difluorophenyl | B2 |
| 16 | N-[[2-[(2R,6S)-2,6-dimethyl-4-morpholinyl]-5-(2,6-dimethyl-4-pyridinyl)-4-thiazolyl]methyl]-cyclopentanecarboxamide | cyclopentyl | B2 |
| 17 | N-[[2-[(2R,6S)-2,6-dimethyl-4-morpholinyl]-5-(2,6-dimethyl-4-pyridinyl)-4-thiazolyl]methyl]-2-methyl-3-pyridinecarboxamide | 2-methyl-3-pyridinyl | B1 |

TABLE 3-continued

Final compounds

| Co. No. | Chemical Name | R1 | Exp. No. |
|---|---|---|---|
| 18 | N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide | 3-methyl-isoxazol-4-yl | B1 |
| 19 | 4-chloro-N-[[2-[(2R,6S)-2,6-dimethyl-4-morpholinyl]-5-(2,6-dimethyl-4-pyridinyl)-4-thiazolyl]methyl]-benzamide | 4-chlorophenyl | B2 |
| 20 | N-[[2-[(2R,6S)-2,6-dimethyl-4-morpholinyl]-5-(2,6-dimethyl-4-pyridinyl)-4-thiazolyl]methyl]-2-methyl-5-(trifluoromethyl)-4-oxazolecarboxamide | 2-methyl-5-(trifluoromethyl)oxazol-4-yl | B1 |
| 21 | N-[[2-[(2R,6S)-2,6-dimethyl-4-morpholinyl]-5-(2,6-dimethyl-4-pyridinyl)-4-thiazolyl]methyl]-2,4-dimethyl-benzamide | 2,4-dimethylphenyl | B1 |
| 22 | 4-chloro-N-[[2-[(2R,6S)-2,6-dimethyl-4-morpholinyl]-5-(2,6-dimethyl-4-pyridinyl)-4-thiazolyl]methyl]-2-methyl-benzamide | 4-chloro-2-methylphenyl | B1 |
| 23 | N-[[2-[(2R,6S)-2,6-dimethyl-4-morpholinyl]-5-(2,6-dimethyl-4-pyridinyl)-4-thiazolyl]methyl]-4-(trifluoromethyl)-benzamide | 4-(trifluoromethyl)phenyl | B1 |
| 24 | N-[[2-[(2R,6S)-2,6-dimethyl-4-morpholinyl]-5-(2,6-dimethyl-4-pyridinyl)-4-thiazolyl]methyl]-4-fluoro-2-methyl-benzamide | 4-fluoro-2-methylphenyl | B1 |
| 25 | N-[[2-[(2R,6S)-2,6-dimethyl-4-morpholinyl]-5-(2,6-dimethyl-4-pyridinyl)-4-thiazolyl]methyl]-3,5-dimethyl-4-isoxazolecarboxamide | 3,5-dimethyl-isoxazol-4-yl | B1 |

TABLE 3-continued

Final compounds

| Co. No. | Chemical Name | R1 | Exp. No. |
|---|---|---|---|
| 26 | 2,3-dichloro-N-[[2-[(2R,6S)-2,6-dimethyl-4-morpholinyl]-5-(2,6-dimethyl-4-pyridinyl)-4-thiazolyl]methyl]-benzamide | 2,3-dichlorophenyl | B1 |
| 27 | N-[[2-[(2R,6S)-2,6-dimethyl-4-morpholinyl]-5-(2,6-dimethyl-4-pyridinyl)-4-thiazolyl]methyl]-benzamide | phenyl | B1 |
| 28 | (3S)-N-[[2-[(2R,6S)-2,6-dimethyl-4-morpholinyl]-5-(2,6-dimethyl-4-pyridinyl)-4-thiazolyl]methyl]tetrahydro-3-furancarboxamide | tetrahydrofuran-3-yl | B1 |
| 29 | N-[[2-[(2R,6S)-2,6-dimethyl-4-morpholinyl]-5-(2,6-dimethyl-4-pyridinyl)-4-thiazolyl]methyl]-2,4-dimethyl-5-thiazolecarboxamide | 2,4-dimethylthiazol-5-yl | B1 |
| 30 | N-[[2-[(2R,6S)-2,6-dimethyl-4-morpholinyl]-5-(2,6-dimethyl-4-pyridinyl)-4-thiazolyl]methyl]-4-methoxy-benzamide | 4-methoxyphenyl | B2 |
| 31 | N-[[2-[(2R,6S)-2,6-dimethyl-4-morpholinyl]-5-(2,6-dimethyl-4-pyridinyl)-4-thiazolyl]methyl]-2-methyl-4-oxazolecarboxamide | 2-methyloxazol-4-yl | B1 |
| 32 | N-[[2-[(2R,6S)-2,6-dimethyl-4-morpholinyl]-5-(2,6-dimethyl-4-pyridinyl)-4-thiazolyl]methyl]-2,3-difluoro-benzamide | 2,3-difluorophenyl | B1 |
| 33 | N-[[2-[(2R,6S)-2,6-dimethyl-4-morpholinyl]-5-(2,6-dimethyl-4-pyridinyl)-4-thiazolyl]methyl]-4-fluoro-3-(trifluoromethyl)-benzamide | 4-fluoro-3-(trifluoromethyl)phenyl | B1 |
| 34 | N-[[2-[(2R,6S)-2,6-dimethyl-4-morpholinyl]-5-(2,6-dimethyl-4-pyridinyl)-4-thiazolyl]methyl]-1-methyl-cyclopropanecarboxamide | 1-methylcyclopropyl | B1 |

TABLE 3-continued

Final compounds

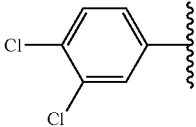 [SMILES: *c1ccc(Cl)c(Cl)c1]

| Co. No. | Chemical Name | R1 | Exp. No. |
|---|---|---|---|
| 35 | 3,4-dichloro-N-[[2-[(2R,6S)-2,6-dimethyl-4-morpholinyl]-5-(2,6-dimethyl-4-pyridinyl)-4-thiazolyl]methyl]-benzamide | 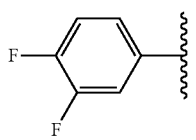 [SMILES: *c1ccc(F)c(F)c1] | B2 |
| 36 | N-[[2-[(2R,6S)-2,6-dimethyl-4-morpholinyl]-5-(2,6-dimethyl-4-pyridinyl)-4-thiazolyl]methyl]-3,4-difluoro-benzamide | 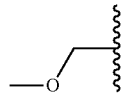 | B2 |
| 37 | N-[[2-[(2R,6S)-2,6-dimethyl-4-morpholinyl]-5-(2,6-dimethyl-4-pyridinyl)-4-thiazolyl]methyl]-2-methoxy-acetamide | 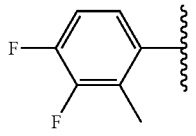 [SMILES: *c1ccc(F)c(F)c1C] | B2 |
| 38 | N-[[2-[(2R,6S)-2,6-dimethyl-4-morpholinyl]-5-(2,6-dimethyl-4-pyridinyl)-4-thiazolyl]methyl]-3,4-difluoro-2-methyl-benzamide |  | B1 |
| 39 | N-[[2-[(2R,6S)-2,6-dimethyl-4-morpholinyl]-5-(2,6-dimethyl-4-pyridinyl)-4-thiazolyl]methyl]-propanamide |  | B2 |
| 40 | N-[[2-[(2R,6S)-2,6-dimethyl-4-morpholinyl]-5-(2,6-dimethyl-4-pyridinyl)-4-thiazolyl]methyl]-2-methyl-propanamide | 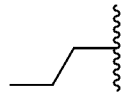 | B2 |
| 41 | N-[[2-[(2R,6S)-2,6-dimethyl-4-morpholinyl]-5-(2,6-dimethyl-4-pyridinyl)-4-thiazolyl]methyl]-butanamide | 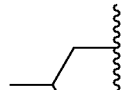 | B2 |
| 42 | N-[[2-[(2R,6S)-2,6-dimethyl-4-morpholinyl]-5-(2,6-dimethyl-4-pyridinyl)-4-thiazolyl]methyl]-3-methyl-butanamide | | B2 |
| 43 | N-[[2-[(2R,6S)-2,6-dimethyl-4-morpholinyl]-5-(2,6-dimethyl-4-pyridinyl)-4-thiazolyl]methyl]-2,2,3,3-tetramethyl-cyclopropanecarboxamide | 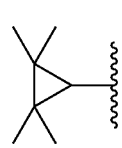 [SMILES: *C1C(C)(C)C1(C)C] | B1 |

TABLE 3-continued

Final compounds

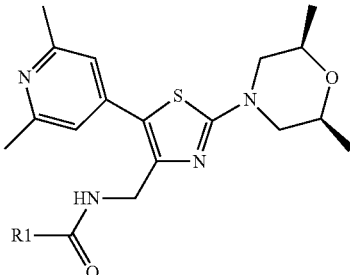

| Co. No. | Chemical Name | R1 | Exp. No. |
|---|---|---|---|
| 44 | N-[[2-[(2R,6S)-2,6-dimethyl-4-morpholinyl]-5-(2,6-dimethyl-4-pyridinyl)-4-thiazolyl]methyl]-3-(trifluoromethyl)-benzamide | 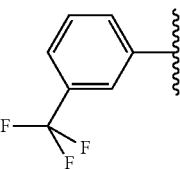 [SMILES: *c1cccc(C(F)(F)F)c1] | B1 |
| 45 | N-[[2-[(2R,6S)-2,6-dimethyl-4-morpholinyl]-5-(2,6-dimethyl-4-pyridinyl)-4-thiazolyl]methyl]-2,2-difluoro-1,3-benzodioxole-5-carboxamide | 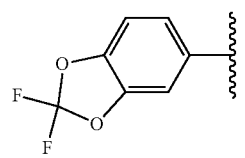 [SMILES: *c1ccc2c(c1)OC(F)(F)O2] | B1 |
| 46 | N-[[2-[(2R,6S)-2,6-dimethyl-4-morpholinyl]-5-(2,6-dimethyl-4-pyridinyl)-4-thiazolyl]methyl]-2,2-difluoro-1,3-benzodioxole-4-carboxamide | 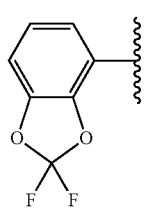 [SMILES: *c1cccc2c1OC(F)(F)O2] | B1 |
| 47 | N-[[2-[(2R,6S)-2,6-dimethyl-4-morpholinyl]-5-(2,6-dimethyl-4-pyridinyl)-4-thiazolyl]methyl]-2,2-dimethyl-propanamide | 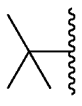 | B3 |
| 48 | N-[[2-[(2R,6S)-2,6-dimethyl-4-morpholinyl]-5-(2,6-dimethyl-4-pyridinyl)-4-thiazolyl]methyl]-cyclopropanecarboxamide | 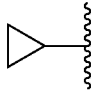 [SMILES: *C1CC1] | B1 |
| 49 | N-[[2-[(2R,6S)-2,6-dimethyl-4-morpholinyl]-5-(2,6-dimethyl-4-pyridinyl)-4-thiazolyl]methyl]-cyclobutaneacetamide | 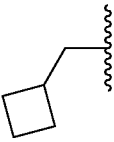 [SMILES: *CC1CCC1] | B1 |
| 50 | N-[[2-[(2R,6S)-2,6-dimethyl-4-morpholinyl]-5-(2,6-dimethyl-4-pyridinyl)-4-thiazolyl]methyl]-cyclopropanepropanamide | 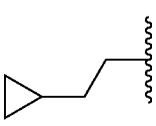 [SMILES: *CCC1CC1] | B1 |
| 51 | N-[[2-[(2R,6S)-2,6-dimethyl-4-morpholinyl]-5-(2,6-dimethyl-4-pyridinyl)-4-thiazolyl]methyl]-4-methyl-pentanamide | 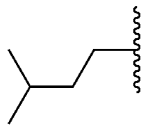 [SMILES: *CCC(C)C] | B1 |

TABLE 3-continued

Final compounds

| Co. No. | Chemical Name | R1 | Exp. No. |
|---|---|---|---|
| 52 | (2S)-N-[[2-[(2R,6S)-2,6-dimethyl-4-morpholinyl]-5-(2,6-dimethyl-4-pyridinyl)-4-thiazolyl]methyl]-1-methyl-2-pyrrolidinecarboxamide | S-enantiomer (1-methyl-2-pyrrolidinyl) | B1 |
| 53 | N-[[2-[(2R,6S)-2,6-dimethyl-4-morpholinyl]-5-(2,6-dimethyl-4-pyridinyl)-4-thiazolyl]methyl]-3-methoxy-propanamide | 3-methoxypropyl | B1 |
| 54 | 3-(1,1-dimethylethyl)-N-[[2-[(2R,6S)-2,6-dimethyl-4-morpholinyl]-5-(2,6-dimethyl-4-pyridinyl)-4-thiazolyl]methyl]-1-methyl-1H-pyrazole-5-carboxamide | 3-tert-butyl-1-methyl-1H-pyrazol-5-yl | B2 |
| 60 | N-[[2-[(2R,6S)-2,6-dimethyl-4-morpholinyl]-5-(2,6-dimethyl-4-pyridinyl)-4-thiazolyl]methyl-acetamide | —CH$_3$ | B3 |
| 127 | 5-cyclopropyl-N-[[2-[(2R,6S)-2,6-dimethyl-4-morpholinyl]-5-(2,6-dimethyl-4-pyridinyl)-4-thiazolyl]methyl]-3-isoxazolecarboxamide | 5-cyclopropyl-3-isoxazolyl | B1 |
| 128 | N-[[2-[(2R,6S)-2,6-dimethyl-4-morpholinyl]-5-(2,6-dimethyl-4-pyridinyl)-4-thiazolyl]methyl]-4,4,4-trifluoro-butanamide, | 3,3,3-trifluoropropyl | B1 |
| 129 | 1-(1,1-dimethylethyl)-N-[[2-[(2R,6S)-2,6-dimethyl-4-morpholinyl]-5-(2,6-dimethyl-4-pyridinyl)-4-thiazolyl]methyl]-3-methyl-1H-pyrazole-5-carboxamide | 1-tert-butyl-3-methyl-1H-pyrazol-5-yl | B2 |
| 130 | N-[[2-[(2R,6S)-2,6-dimethyl-4-morpholinyl]-5-(2,6-dimethyl-4-pyridinyl)-4-thiazolyl]methyl]-1,2-benzisoxazole-3-carboxamide | 1,2-benzisoxazol-3-yl | B1 |

TABLE 3-continued

Final compounds

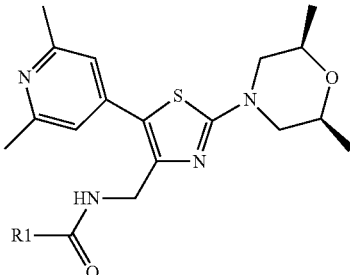

| Co. No. | Chemical Name | R1 | Exp. No. |
|---|---|---|---|
| 131 | N-[[2-[(2R,6S)-2,6-dimethyl-4-morpholinyl]-5-(2,6-dimethyl-4-pyridinyl)-4-thiazolyl]methyl]-1,5-dimethyl-1H-pyrazole-3-carboxamide | 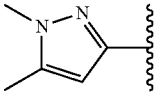 [SMILES: *c1cc(C)n(C)n1] | B2 |
| 132 | N-[[2-[(2R,6S)-2,6-dimethyl-4-morpholinyl]-5-(2,6-dimethyl-4-pyridinyl)-4-thiazolyl]methyl]-4-oxazolecarboxamide | 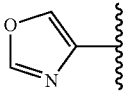 | B1 |
| 134 | N-[[2-[(2R,6S)-2,6-dimethyl-4-morpholinyl]-5-(2,6-dimethyl-4-pyridinyl)-4-thiazolyl]methyl]-2,5-dimethyl-4-oxazolecarboxamide | 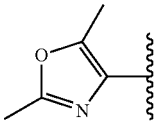 | B1 |
| 135 | N-[[2-[(2R,6S)-2,6-dimethyl-4-morpholinyl]-5-(2,6-dimethyl-4-pyridinyl)-4-thiazolyl]methyl]-5-(1-methylethyl)-3-isoxazolecarboxamide | 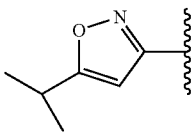 [SMILES: *c1cc(C(C)C)on1] | B1 |
| 136 | N-[[2-[(2R,6S)-2,6-dimethyl-4-morpholinyl]-5-(2,6-dimethyl-4-pyridinyl)-4-thiazolyl]methyl]-1,3-dimethyl-1H-pyrazole-5-carboxamide | 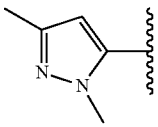 | B2 |
| 137 | N-[[2-[(2R,6S)-2,6-dimethyl-4-morpholinyl]-5-(2,6-dimethyl-4-pyridinyl)-4-thiazolyl]methyl]-2-pyridinecarboxamide | 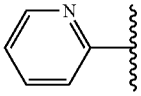 | B1 |
| 138 | N-[[2-[(2R,6S)-2,6-dimethyl-4-morpholinyl]-5-(2,6-dimethyl-4-pyridinyl)-4-thiazolyl]methyl]-2-pyrazinecarboxamide | 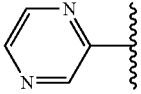 | B2 |
| 139 | 1-(1,1-dimethylethyl)-N-[[2-[(2R,6S)-2,6-dimethyl-4-morpholinyl]-5-(2,6-dimethyl-4-pyridinyl)-4-thiazolyl]methyl]-5-methyl-1H-pyrazole-3-carboxamide | 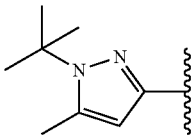 [SMILES: *c1cc(C)n(C(C)(C)C)n1] | B2 |
| 140 | N-[[2-[(2R,6S)-2,6-dimethyl-4-morpholinyl]-5-(2,6-dimethyl-4-pyridinyl)-4-thiazolyl]methyl]-6-methoxy-2-pyridinecarboxamide | 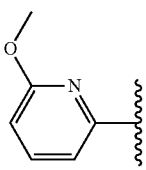 [SMILES: *c1cccc(OC)n1] | B1 |

TABLE 3-continued

Final compounds

| Co. No. | Chemical Name | R1 | Exp. No. |
|---|---|---|---|
| 141 | N-[[2-[(2R,6S)-2,6-dimethyl-4-morpholinyl]-5-(2,6-dimethyl-4-pyridinyl)-4-thiazolyl]methyl]-3-furancarboxamide | | B2 |
| 142 | N-[[2-[(2R,6S)-2,6-dimethyl-4-morpholinyl]-5-(2,6-dimethyl-4-pyridinyl)-4-thiazolyl]methyl]-1-methyl-1H-pyrazole-3-carboxamide | | B1 |
| 143 | 5-(1,1-dimethylethyl)-N-[[2-[(2R,6S)-2,6-dimethyl-4-morpholinyl]-5-(2,6-dimethyl-4-pyridinyl)-4-thiazolyl]methyl]-3-isoxazolecarboxamide | | B1 |
| 144 | 4-(aminosulfonyl)-N-[[2-[(2R,6S)-2,6-dimethyl-4-morpholinyl]-5-(2,6-dimethyl-4-pyridinyl)-4-thiazolyl]methyl]-benzamide | | B1 |
| 145 | N-[[2-[(2R,6S)-2,6-dimethyl-4-morpholinyl]-5-(2,6-dimethyl-4-pyridinyl)-4-thiazolyl] methyl]-5,5,5-trifluoro-pentanamide | | B1 |
| 146 | N-[[2-[(2R,6S)-2,6-dimethyl-4-morpholinyl]-5-(2,6-dimethyl-4-pyridinyl)-4-thiazolyl]methyl]-2,5-dimethyl-3-furancarboxamide | | B2 |
| 147 | N-[[2-[(2R,6S)-2,6-dimethyl-4-morpholinyl]-5-(2,6-dimethyl-4-pyridinyl)-4-thiazolyl]methyl]-3-methyl-2-furancarboxamide | | B1 |
| 148 | N-[[2-[(2R,6S)-2,6-dimethyl-4-morpholinyl]-5-(2,6-dimethyl-4-pyridinyl)-4-thiazolyl]methyl]-4-methyl-5-isoxazolecarboxamide | | B1 |

TABLE 3-continued

Final compounds

| Co. No. | Chemical Name | R1 | Exp. No. |
|---|---|---|---|
| 149 | N-[[2-[(2R,6S)-2,6-dimethyl-4-morpholinyl]-5-(2,6-dimethyl-4-pyridinyl)-4-thiazolyl]methyl]-5-isoxazolecarboxamide | isoxazol-5-yl | B1 |
| 150 | N-[[2-[(2R,6S)-2,6-dimethyl-4-morpholinyl]-5-(2,6-dimethyl-4-pyridinyl)-4-thiazolyl]methyl]-3-methyl-2-thiophenecarboxamide | 3-methylthiophen-2-yl | B1 |
| 151 | N-[[2-[(2R,6S)-2,6-dimethyl-4-morpholinyl]-5-(2,6-dimethyl-4-pyridinyl)-4-thiazolyl]methyl]-2-methyl-3-furancarboxamide | 2-methylfuran-3-yl | B1 |
| 152 | N-[[2-[(2R,6S)-2,6-dimethyl-4-morpholinyl]-5-(2,6-dimethyl-4-pyridinyl)-4-thiazolyl]methyl]-4-methyl-5-oxazolecarboxamide | 4-methyloxazol-5-yl | B1 |
| 153 | N-[[2-[(2R,6S)-2,6-dimethyl-4-morpholinyl]-5-(2,6-dimethyl-4-pyridinyl)-4-thiazolyl]methyl]-4-methyl-5-thiazolecarboxamide | 4-methylthiazol-5-yl | B1 |
| 154 | N-[[2-[(2R,6S)-2,6-dimethyl-4-morpholinyl]-5-(2,6-dimethyl-4-pyridinyl)-4-thiazolyl]methyl]tetrahydro-2,2-dimethyl-5-oxo-3-furancarboxamide | tetrahydro-2,2-dimethyl-5-oxofuran-3-yl | B1 |
| 155 | N-[[2-[(2R,6S)-2,6-dimethyl-4-morpholinyl]-5-(2,6-dimethyl-4-pyridinyl)-4-thiazolyl]methyl]-4-methyl-1,2,3-thiadiazole-5-carboxamide | 4-methyl-1,2,3-thiadiazol-5-yl | B2 |
| 158 | N-[[2-[(2R,6S)-2,6-dimethyl-4-morpholinyl]-5-(2,6-dimethyl-4-pyridinyl)-4-thiazolyl]methyl]-2-methoxy-4-methyl-5-thiazolecarboxamide | 2-methoxy-4-methylthiazol-5-yl | B1 |
| 159 | N-[[2-[(2R,6S)-2,6-dimethyl-4-morpholinyl]-5-(2,6-dimethyl-4-pyridinyl)-4-thiazolyl]methyl]-2,4-dimethyl-5-oxazolecarboxamide | 2,4-dimethyloxazol-5-yl | B1 |

TABLE 3-continued

Final compounds

| Co. No. | Chemical Name | R1 | Exp. No. |
|---|---|---|---|
| 160 | N-[[2-[(2R,6S)-2,6-dimethyl-4-morpholinyl]-5-(2,6-dimethyl-4-pyridinyl)-4-thiazolyl]methyl]-1,5-dimethyl-1H-pyrazole-4-carboxamide | 1,5-dimethyl-1H-pyrazol-4-yl | B1 |
| 161 | N-[[2-[(2R,6S)-2,6-dimethyl-4-morpholinyl]-5-(2,6-dimethyl-4-pyridinyl)-4-thiazolyl]methyl]-5-methyl-4-oxazolecarboxamide | 5-methyl-oxazol-4-yl | B1 |
| 162 | N-[[2-[(2R,6S)-2,6-dimethyl-4-morpholinyl]-5-(2,6-dimethyl-4-pyridinyl)-4-thiazolyl]methyl]-2,5-dimethyl-3-thiophenecarboxamide | 2,5-dimethyl-thiophen-3-yl | B1 |
| 163 | N-[[2-[(2R,6S)-2,6-dimethyl-4-morpholinyl]-5-(2,6-dimethyl-4-pyridinyl)-4-thiazolyl]methyl]-3-methyl-5-(trifluoromethyl)-4-isoxazolecarboxamide | 3-methyl-5-(trifluoromethyl)-isoxazol-4-yl | B1 |
| 164 | N-[[2-[(2R,6S)-2,6-dimethyl-4-morpholinyl]-5-(2,6-dimethyl-4-pyridinyl)-4-thiazolyl]methyl]-4,5-dimethyl-3-thiophenecarboxamide | 4,5-dimethyl-thiophen-3-yl | B1 |
| 165 | N-[[2-[(2R,6S)-2,6-dimethyl-4-morpholinyl]-5-(2,6-dimethyl-4-pyridinyl)-4-thiazolyl]methyl]-2-methyl-6-(trifluoromethyl)-3-pyridinecarboxamide, | 2-methyl-6-(trifluoromethyl)-pyridin-3-yl | B1 |
| 166 | N-[[2-[(2R,6S)-2,6-dimethyl-4-morpholinyl]-5-(2,6-dimethyl-4-pyridinyl)-4-thiazolyl]methyl]-3,5-dimethyl-4-isoxazoleacetamide, | 3,5-dimethyl-isoxazol-4-yl-CH2 | B1 |

TABLE 3-continued

Final compounds

| Co. No. | Chemical Name | R1 | Exp. No. |
|---|---|---|---|
| 167 | N-[[2-[(2R,6S)-2,6-dimethyl-4-morpholinyl]-5-(2,6-dimethyl-4-pyridinyl)-4-thiazolyl]methyl]-3-methyl-5-isoxazoleacetamide, | 3-methyl-5-isoxazolyl-CH2- | B1 |
| 168 | N-[[2-[(2R,6S)-2,6-dimethyl-4-morpholinyl]-5-(2,6-dimethyl-4-pyridinyl)-4-thiazolyl]methyl]-3,3,3-trifluoro-propanamide | CF3-CH2- | B1 |
| 169 | N-[[2-[(2R,6S)-2,6-dimethyl-4-morpholinyl]-5-(2,6-dimethyl-4-pyridinyl)-4-thiazolyl]methyl]-1,3-dimethyl-1H-pyrazole-4-carboxamide | 1,3-dimethyl-1H-pyrazol-4-yl | B1 |
| 170 | 2-cyano-N-[[2-[(2R,6S)-2,6-dimethyl-4-morpholinyl]-5-(2,6-dimethyl-4-pyridinyl)-4-thiazolyl]methyl]-acetamide | NC-CH2- | B1 |
| 171 | N-[[2-[(2R,6S)-2,6-dimethyl-4-morpholinyl]-5-(2,6-dimethyl-4-pyridinyl)-4-thiazolyl]methyl]-3,4-dimethyl-5-isoxazolecarboxamide | 3,4-dimethyl-5-isoxazolyl | B1 |
| 172 | N-[[2-[(2R,6S)-2,6-dimethyl-4-morpholinyl]-5-(2,6-dimethyl-4-pyridinyl)-4-thiazolyl]methyl]-1,4-dimethyl-1H-pyrazole-3-carboxamide | 1,4-dimethyl-1H-pyrazol-3-yl | B1 |
| 173 | N-[[2-[(2R,6S)-2,6-dimethyl-4-morpholinyl]-5-(2,6-dimethyl-4-pyridinyl)-4-thiazolyl]methyl]-3,5-dimethyl-2-furancarboxamide | 3,5-dimethyl-2-furyl | B1 |
| 174 | N-[[2-[(2R,6S)-2,6-dimethyl-4-morpholinyl]-5-(2,6-dimethyl-4-pyridinyl)-4-thiazolyl]methyl]-4-methyl-3-isoxazolecarboxamide | 4-methyl-3-isoxazolyl | B1 |

TABLE 3-continued

Final compounds

| Co. No. | Chemical Name | R1 | Exp. No. |
|---|---|---|---|
| 175 | N-[[2-[(2R,6S)-2,6-dimethyl-4-morpholinyl]-5-(2,6-dimethyl-4-pyridinyl)-4-thiazolyl]methyl]-2-(2,2,2-trifluoroethoxy)-acetamide | 2,2,2-trifluoroethoxymethyl | B1 |
| 176 | N-[[2-[(2R,6S)-2,6-dimethyl-4-morpholinyl]-5-(2,6-dimethyl-4-pyridinyl)-4-thiazolyl]methyl]-1-hydroxy-cyclopropanecarboxamide | 1-hydroxycyclopropyl | B1 |
| 177 | N-[[2-[(2R,6S)-2,6-dimethyl-4-morpholinyl]-5-(2,6-dimethyl-4-pyridinyl)-4-thiazolyl]methyl]-2,2,2-trifluoro-acetamide | CF$_3$ | B3 |
| 178 | N-[[2-[(2R,6S)-2,6-dimethyl-4-morpholinyl]-5-(2,6-dimethyl-4-pyridinyl)-4-thiazolyl]methyl]-5-methyl-4-thiazolecarboxamide | 5-methyl-4-thiazolyl | B1 |
| 179 | N-[[2-[(2R,6S)-2,6-dimethyl-4-morpholinyl]-5-(2,6-dimethyl-4-pyridinyl)-4-thiazolyl]methyl]-α-methyl-cyclopropaneacetamide | 1-cyclopropylethyl | B1 |
| 180 | N-[[2-[(2R,6S)-2,6-dimethyl-4-morpholinyl]-5-(2,6-dimethyl-4-pyridinyl)-4-thiazolyl]methyl]-3-isoxazolecarboxamide | 3-isoxazolyl | B1 |

TABLE 4

Final compounds (S* means S or R; R* means R or S)

| Co. No. | Chemical Name | R1 | X | Exp. No. |
|---|---|---|---|---|
| 55 | N-[[2-[2,6-dimethyl-4-morpholinyl]-5-(2,6-dimethyl-4-pyridinyl)-4-thiazolyl]methyl]-cyclopropaneacetamide (racemic trans mixture) | cyclopropylmethyl | 2,6-dimethylmorpholin-4-yl | B1, from Int. No. 16 |
| 56 | N-[[2-[2,6-dimethyl-4-morpholinyl]-5-(2,6-dimethyl-4-pyridinyl)-4-thiazolyl]methyl]-4-fluoro-2-methyl-benzamide (racemic trans mixture) | 4-fluoro-2-methylphenyl | 2,6-dimethylmorpholin-4-yl | B1, from Int. No. 16 |
| 57 | N-[[2-[2,6-dimethyl-4-morpholinyl]-5-(2,6-dimethyl-4-pyridinyl)-4-thiazolyl]methyl]-cyclobutanecarboxamide (racemic trans mixture) | cyclobutyl | 2,6-dimethylmorpholin-4-yl | B2, from Int. No. 16 |
| 58 | 4-chloro-N-[[2-[2,6-dimethyl-4-morpholinyl]-5-(2,6-dimethyl-4-pyridinyl)-4-thiazolyl]methyl]-benzamide (racemic trans mixture) | 4-chlorophenyl | 2,6-dimethylmorpholin-4-yl | B2, from Int. No. 16 |
| 59 | N-[[2-[2,6-dimethyl-4-morpholinyl]-5-(2,6-dimethyl-4-pyridinyl)-4-thiazolyl]methyl]-5-methyl-3-isoxazolecarboxamide (racemic trans mixture) | 5-methylisoxazol-3-yl | 2,6-dimethylmorpholin-4-yl | B1, from Int. No. 16 |
| 61 | N-[[2-[2,6-dimethyl-4-morpholinyl]-5-(2,6-dimethyl-4-pyridinyl)-4-thiazolyl]methyl]-butanamide (racemic trans mixture) | propyl | 2,6-dimethylmorpholin-4-yl | B2, from Int. No. 16 |
| 62 | N-[[5-(2,6-dimethyl-4-pyridinyl)-2-(4-morpholinyl)-4-thiazolyl]methyl]-3-methyl-4-isoxazolecarboxamide | 3-methylisoxazol-4-yl | morpholin-4-yl | B1, from Int. No. 15 |
| 63 | N-[[5-(2,6-dimethyl-4-pyridinyl)-2-(4-morpholinyl)-4-thiazolyl]methyl]-5-methyl-3-isoxazolecarboxamide | 5-methylisoxazol-3-yl | morpholin-4-yl | B1, from Int. No. 15 |

TABLE 4-continued

Final compounds (S* means S or R; R* means R or S)

| Co. No. | Chemical Name | R1 | X | Exp. No. |
|---|---|---|---|---|
| 64 | N-[[5-(2,6-dimethyl-4-pyridinyl)-2-(4-morpholinyl)-4-thiazolyl]methyl]-cyclopropaneacetamide | cyclopropylmethyl | morpholinyl | B1, from Int. No. 15 |
| 65 | N-[[5-(2,6-dimethyl-4-pyridinyl)-2-(4-morpholinyl)-4-thiazolyl]methyl]-cyclobutanecarboxamide | cyclobutyl | morpholinyl | B2, from Int. No. 15 |
| 66 | N-[[5-(2,6-dimethyl-4-pyridinyl)-2-(4-morpholinyl)-4-thiazolyl]methyl]-4-fluoro-benzamide | 4-fluorophenyl | morpholinyl | B2, from Int. No. 15 |
| 67 | N-[[5-(2,6-dimethyl-4-pyridinyl)-2-(4-morpholinyl)-4-thiazolyl]methyl]-butanamide | propyl | morpholinyl | B2, from Int. No. 15 |
| 68 | N-[[2-[2,6-dimethyl-4-morpholinyl]-5-(2,6-dimethyl-4-pyridinyl)-4-thiazolyl]methyl]-3-methyl-4-isoxazolecarboxamide (racemic trans mixture) | 3-methyl-4-isoxazolyl | 2,6-dimethyl-morpholinyl | B1, from Int. No. 16 |
| 69 | N-[[5-(2,6-dimethyl-4-pyridinyl)-2-[(2S*)-2-methyl-4-morpholinyl]-4-thiazolyl]methyl]-3-methyl-4-isoxazolecarboxamide | 3-methyl-4-isoxazolyl | (2S*)-2-methyl-morpholinyl | B1, from Int. No. 21 |
| 70 | N-[[5-(2,6-dimethyl-4-pyridinyl)-2-[(2S*)-2-methyl-4-morpholinyl]-4-thiazolyl]methyl]-4-fluoro-2-methyl-benzamide | 4-fluoro-2-methyl-phenyl | (2S*)-2-methyl-morpholinyl | B1, from Int. No. 21 |
| 71 | N-[[5-(2,6-dimethyl-4-pyridinyl)-2-[(2S*)-2-methyl-4-morpholinyl]-4-thiazolyl]methyl]-2-methyl-propanamide | isopropyl | (2S*)-2-methyl-morpholinyl | B2, from Int. No. 21 |
| 72 | N-[[5-(2,6-dimethyl-4-pyridinyl)-2-[(2S*)-2-methyl-4-morpholinyl]-4-thiazolyl]methyl]-3-methyl-5-isoxazolecarboxamide | 3-methyl-5-isoxazolyl | (2S*)-2-methyl-morpholinyl | B2, from Int. No. 21 |

TABLE 4-continued

Final compounds (S* means S or R; R* means R or S)

| Co. No. | Chemical Name | R1 | X | Exp. No. |
|---|---|---|---|---|
| 73 | N-[[5-(2,6-dimethyl-4-pyridinyl)-2-[(2R*)-2-methyl-4-morpholinyl]-4-thiazolyl]methyl]-3-methyl-4-isoxazolecarboxamide | 3-methyl-isoxazol-4-yl | (R*)-2-methyl-morpholin-4-yl | B1, from Intermediate No. 20 |
| 74 | N-[[5-(2,6-dimethyl-4-pyridinyl)-2-[(2R*)-2-methyl-4-morpholinyl]-4-thiazolyl]methyl]-5-methyl-3-isoxazolecarboxamide, | 5-methyl-isoxazol-3-yl | (R*)-2-methyl-morpholin-4-yl | B1, from Int. No. 20 |
| 75 | N-[[5-(2,6-dimethyl-4-pyridinyl)-2-[(2R*)-2-methyl-4-morpholinyl]-4-thiazolyl]methyl]-cyclopropaneacetamide | cyclopropylmethyl | (R*)-2-methyl-morpholin-4-yl | B1, from Int. No. 20 |
| 76 | N-[[5-(2,6-dimethyl-4-pyridinyl)-2-[(2R*)-2-methyl-4-morpholinyl]-4-thiazolyl]methyl]-2-methyl-propanamide | isopropyl | (R*)-2-methyl-morpholin-4-yl | B2, from Int. No. 20 |
| 77 | N-[[5-(2,6-dimethyl-4-pyridinyl)-2-[(2R*)-2-methyl-4-morpholinyl]-4-thiazolyl]methyl]-4-fluoro-2-methyl-benzamide | 4-fluoro-2-methyl-phenyl | (R*)-2-methyl-morpholin-4-yl | B1, from Int. No. 20 |
| 78 | N-[[5-(2,6-dimethyl-4-pyridinyl)-2-[(2S*)-2-methyl-4-morpholinyl]-4-thiazolyl]methyl]-cyclopropaneacetamide | cyclopropylmethyl | (S*)-2-methyl-morpholin-4-yl | B1, from Int. No. 21 |
| 79 | N-[[5-(2,6-dimethyl-4-pyridinyl)-2-[(2S*)-2-methyl-4-morpholinyl)-4-thiazolyl]methyl]-5-methyl-3-isoxazolecarboxamide | 5-methyl-isoxazol-3-yl | (S*)-2-methyl-morpholin-4-yl | B1, from Int. No. 21 |
| 80 | N-[[5-(2,6-dimethyl-4-pyridinyl)-2-(4-morpholinyl)-4-thiazolyl]methyl]-4-fluoro-2-methyl-benzamide | 4-fluoro-2-methyl-phenyl | morpholin-4-yl | B1, from Int. No. 15 |

TABLE 4-continued

Final compounds (S* means S or R; R* means R or S)

| Co. No. | Chemical Name | R1 | X | Exp. No. |
|---|---|---|---|---|
| 133 | N-[[5-(2,6-dimethyl-4-pyridinyl)-2-[2-methyl-6-(trifluoromethyl)-4-morpholinyl]-4-thiazolyl]methyl]-cyclopropaneacetamide (trans B enantiomer) | cyclopropylmethyl | 2-methyl-6-(trifluoromethyl)morpholin-4-yl | B5, Chiral separation of co. No 205 |
| 156 | N-[[2-(2,2-dimethyl-4-morpholinyl)-5-(2,6-dimethyl-4-pyridinyl)-4-thiazolyl]methyl]-cyclopropaneacetamide | cyclopropylmethyl | 2,2-dimethylmorpholin-4-yl | B1, from Int. No. 23 |
| 157 | N-[[2-(2,2-dimethyl-4-morpholinyl)-5-(2,6-dimethyl-4-pyridinyl)-4-thiazolyl]methyl]-4-fluoro-2-methyl-benzamide | 4-fluoro-2-methylphenyl | 2,2-dimethylmorpholin-4-yl | B1, from Int. No. 23 |
| 181 | N-[[2-(2,2-dimethyl-4-morpholinyl)-5-(2,6-dimethyl-4-pyridinyl)-4-thiazolyl]methyl]-5-methyl-3-isoxazolecarboxamide | 5-methylisoxazol-3-yl | 2,2-dimethylmorpholin-4-yl | B2, from Int. No. 23 |
| 182 | N-[[2-(2,2-dimethyl-4-morpholinyl)-5-(2,6-dimethyl-4-pyridinyl)-4-thiazolyl]methyl]-3-methyl-4-isoxazolecarboxamide•HCl | 3-methylisoxazol-4-yl | 2,2-dimethylmorpholin-4-yl | B1, from Int. No. 23 |
| 183 | N-[[2-(2,2-dimethyl-4-morpholinyl)-5-(2,6-dimethyl-4-pyridinyl)-4-thiazolyl]methyl]-2-methyl-propanamide | isopropyl | 2,2-dimethylmorpholin-4-yl | B2, from Int. No. 23 |
| 184 | N-[[5-(2,6-dimethyl-4-pyridinyl)-2-[(3S)-3-methyl-4-morpholinyl]-4-thiazolyl]methyl]-4-fluoro-2-methyl-benzamide | 4-fluoro-2-methylphenyl | (3S)-3-methylmorpholin-4-yl | B1, from Int. No. 24 |
| 185 | N-[[5-(2,6-dimethyl-4-pyridinyl)-2-[(3S)-3-methyl-4-morpholinyl]-4-thiazolyl]methyl]-3-methyl-4-isoxazolecarboxamide | 3-methylisoxazol-4-yl | (3S)-3-methylmorpholin-4-yl | B1, from Int. No. 24 |

TABLE 4-continued

Final compounds (S* means S or R; R* means R or S)

| Co. No. | Chemical Name | R1 | X | Exp. No. |
|---|---|---|---|---|
| 186 | N-[[5-(2,6-dimethyl-4-pyridinyl)-2-[(3S)-3-methyl-4-morpholinyl]-4-thiazolyl]methyl]-5-methyl-3-isoxazolecarboxamide | 5-methyl-isoxazol-3-yl | (3S)-3-methylmorpholin-4-yl | B2, from Int. No. 24 |
| 187 | N-[[5-(2,6-dimethyl-4-pyridinyl)-2-[(3S)-3-methyl-4-morpholinyl]-4-thiazolyl]methyl]-cyclopropaneacetamide | cyclopropylmethyl | (3S)-3-methylmorpholin-4-yl | B1, from Int. No. 24 |
| 188 | N-[[5-(2,6-dimethyl-4-pyridinyl)-2-[(3S)-3-methyl-4-morpholinyl]-4-thiazolyl]methyl]-2-methyl-propanamide | isopropyl | (3S)-3-methylmorpholin-4-yl | B2, from Int. No. 24 |
| 189 | N-[[5-(2,6-dimethyl-4-pyridinyl)-2-[(3S)-3-methyl-4-morpholinyl]-4-thiazolyl]methyl]-3-methyl-butanamide | isobutyl | (3S)-3-methylmorpholin-4-yl | B2, from Int. No. 24 |
| 190 | N-[[5-(2,6-dimethyl-4-pyridinyl)-2-[2-(trifluoromethyl)-4-morpholinyl]-4-thiazolyl]methyl]-cyclopropaneacetamide | cyclopropylmethyl | 2-(trifluoromethyl)morpholin-4-yl | B1, from Int. No. 27 |
| 191 | N-[[5-(2,6-dimethyl-4-pyridinyl)-2-[(2R)-2-(trifluoromethyl)-4-morpholinyl]-4-thiazolyl]methyl]-cyclopropaneacetamide | cyclopropylmethyl | (2R)-2-(trifluoromethyl)morpholin-4-yl | B6, Chiral separation of co No |
| 192 | N-[[5-(2,6-dimethyl-4-pyridinyl)-2-[(2S)-2-(trifluoromethyl)-4-morpholinyl]-4-thiazolyl]methyl]-cyclopropaneacetamide | cyclopropylmethyl | (2S)-2-(trifluoromethyl)morpholin-4-yl | B6, Chiral separation of co No 190 |

TABLE 4-continued

Final compounds (S* means S or R; R* means R or S)

| Co. No. | Chemical Name | R1 | X | Exp. No. |
|---|---|---|---|---|
| 193 | N-[[5-(2,6-dimethyl-4-pyridinyl)-2-[2-(trifluoromethyl)-4-morpholinyl]-4-thiazolyl]methyl]-4-fluoro-2-methyl-benzamide | 4-fluoro-2-methylphenyl | 2-(trifluoromethyl)morpholin-4-yl | B1, from Int. No. 27 |
| 194 | N-[[5-(2,6-dimethyl-4-pyridinyl)-2-[2-(trifluoromethyl)-4-morpholinyl]-4-thiazolyl]methyl]-2-methyl-propanamide | isopropyl | 2-(trifluoromethyl)morpholin-4-yl | B2, from Int. No. 27 |
| 195 | N-[[5-(2,6-dimethyl-4-pyridinyl)-2-[2-(trifluoromethyl)-4-morpholinyl]-4-thiazolyl]methyl]-5-methyl-3-isoxazolecarboxamide | 5-methylisoxazol-3-yl | 2-(trifluoromethyl)morpholin-4-yl | B2, from Int. No. 27 |
| 196 | N-[[5-(2,6-dimethyl-4-pyridinyl)-2-[2-(trifluoromethyl)-4-morpholinyl]-4-thiazolyl]methyl]-3-methyl-4-isoxazolecarboxamide | 3-methylisoxazol-4-yl | 2-(trifluoromethyl)morpholin-4-yl | B1, from Int. No. 27 |
| 202 | N-[[5-(2,6-dimethyl-4-pyridinyl)-2-[2-methyl-6-(trifluoromethyl)-4-morpholinyl]-4-thiazolyl]methyl]-cyclopropaneacetamide (racemic cis mixture) | cyclopropylmethyl | 2-methyl-6-(trifluoromethyl)morpholin-4-yl | B1, from Int. No. 25 |
| 203 | N-[[5-(2,6-dimethyl-4-pyridinyl)-2-[(2R,6R)-2-methyl-6-(trifluoromethyl)-4-morpholinyl]-4-thiazolyl]methyl]-cyclopropaneacetamide | cyclopropylmethyl | (2R,6R)-2-methyl-6-(trifluoromethyl)morpholin-4-yl | B4, Chiral separation of co. No 202 |

TABLE 4-continued

Final compounds (S* means S or R; R* means R or S)

| Co. No. | Chemical Name | R1 | X | Exp. No. |
|---|---|---|---|---|
| 204 | N-[[5-(2,6-dimethyl-4-pyridinyl)-2-[(2S,6S)-2-methyl-6-(trifluoromethyl)-4-morpholinyl]-4-thiazolyl]methyl]-cyclopropaneacetamide | cyclopropylmethyl | (2S,6S)-2-methyl-6-(trifluoromethyl)-4-morpholinyl | B4, Chiral separation of co. No 202 |
| 205 | N-[[5-(2,6-dimethyl-4-pyridinyl)-2-[2-methyl-6-(trifluoromethyl)-4-morpholinyl]-4-thiazolyl]methyl]-cyclopropaneacetamide (racemic trans mixture) | cyclopropylmethyl | 2-methyl-6-(trifluoromethyl)-4-morpholinyl | B1, from Int. No. 26 |
| 206 | N-[[5-(2,6-dimethyl-4-pyridinyl)-2-[2-methyl-6-(trifluoromethyl)-4-morpholinyl]-4-thiazolyl]methyl]-cyclopropaneacetamide (trans A enantiomer) | cyclopropylmethyl | 2-methyl-6-(trifluoromethyl)-4-morpholinyl | B5, Chiral separation of co. No 205 |
| 207 | N-[[5-(2,6-dimethyl-4-pyridinyl)-2-(8-oxa-3-azabicyclo[3.2.1]oct-3-yl)-4-thiazolyl]methyl]-2-methyl-propanamide | isopropyl | 8-oxa-3-azabicyclo[3.2.1]oct-3-yl | B2, from Int. No. 28 |
| 208 | N-[[5-(2,6-dimethyl-4-pyridinyl)-2-(8-oxa-3-azabicyclo[3.2.1]oct-3-yl)-4-thiazolyl]methyl]-4-fluoro-2-methyl-benzamide | 4-fluoro-2-methylphenyl | 8-oxa-3-azabicyclo[3.2.1]oct-3-yl | B1, from Int. No. 28 |
| 209 | N-[[5-(2,6-dimethyl-4-pyridinyl)-2-(8-oxa-3-azabicyclo[3.2.1]oct-3-yl)-4-thiazolyl]methyl]-cyclopropaneacetamide | cyclopropylmethyl | 8-oxa-3-azabicyclo[3.2.1]oct-3-yl | B1, from Int. No. 28 |
| 210 | N-[[5-(2,6-dimethyl-4-pyridinyl)-2-(8-oxa-3-azabicyclo[3.2.1]oct-3-yl)-4-thiazolyl]methyl]-5-methyl-3-isoxazolecarboxamide | 5-methyl-3-isoxazolyl | 8-oxa-3-azabicyclo[3.2.1]oct-3-yl | B2, from Int. No. 28 |

TABLE 4-continued

Final compounds (S* means S or R; R* means R or S)

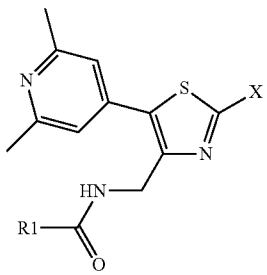

| Co. No. | Chemical Name | R1 | X | Exp. No. |
|---|---|---|---|---|
| 211 | N-[[5-(2,6-dimethyl-4-pyridinyl)-2-(8-oxa-3-azabicyclo[3.2.1]oct-3-yl)-4-thiazolyl]methyl]-3-methyl-4-isoxazolecarboxamide | 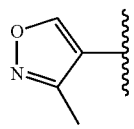 | 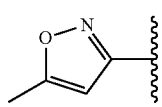 [SMILES: *c1cc(C)on1] | B1, from Int. No. 28 |

TABLE 5

Final compounds

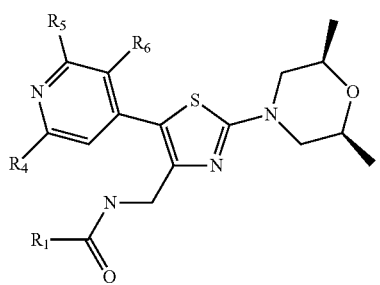

| Co. No. | Chemical Name | R1 | R4 | R5 | R6 | Exp. No. |
|---|---|---|---|---|---|---|
| 81 | N-[[2-[(2R,6S)-2,6-dimethyl-4-morpholinyl]-5-(2-methoxy-6-methyl-4-pyridinyl)-4-thiazolyl]methyl]-3-methyl-4-isoxazolecarboxamide | 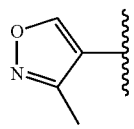 | $CH_3$ | $OCH_3$ | H | B1, from Int. No. 10 |
| 82 | N-[[2-[(2R,6S)-2,6-dimethyl-4-morpholinyl]-5-(2-methoxy-6-methyl-4-pyridinyl)-4-thiazolyl]methyl]-5-methyl-3-isoxazolecarboxamide | 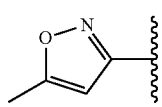 [SMILES: *c1cc(C)on1] | $CH_3$ | $OCH_3$ | H | B1, from Int. No. 10 |
| 83 | N-[[2-[(2R,6S)-2,6-dimethyl-4-morpholinyl]-5-(2-methoxy-6-methyl-4-pyridinyl)-4-thiazolyl]methyl]-cyclopropaneacetamide | 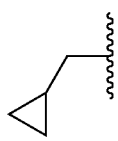 [SMILES: *CC1CC1] | $CH_3$ | $OCH_3$ | H | B1, from Int. No. 10 |
| 84 | N-[[2-[(2R,6S)-2,6-dimethyl-4-morpholinyl]-5-(2-methoxy-6-methyl-4-pyridinyl)-4-thiazolyl]methyl]-cyclobutanecarboxamide | 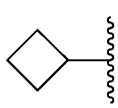 | $CH_3$ | $OCH_3$ | H | B2, from Int. No. 10 |

TABLE 5-continued

Final compounds

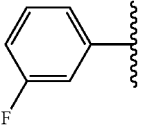

| Co. No. | Chemical Name | R1 | R4 | R5 | R6 | Exp. No. |
|---|---|---|---|---|---|---|
| 85 | N-[[2-[(2R,6S)-2,6-dimethyl-4-morpholinyl]-5-(2-methoxy-6-methyl-4-pyridinyl)-4-thiazolyl]methyl]-3-fluoro-benzamide | 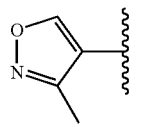 | CH$_3$ | OCH$_3$ | H | B2, from Int. No. 10 |
| 86 | N-[[2-[(2R,6S)-2,6-dimethyl-4-morpholinyl]-5-(2-methyl-4-pyridinyl)-4-thiazolyl]methyl]-3-methyl-4-isoxazolecarboxamide | 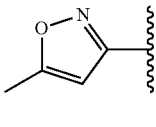 [SMILES: *c1cc(C)on1] | CH$_3$ | H | H | B1, from Int. No. 11 |
| 87 | N-[[2-[(2R,6S)-2,6-dimethyl-4-morpholinyl]-5-(2-methyl-4-pyridinyl)-4-thiazolyl]methyl]-5-methyl-3-isoxazolecarboxamide | 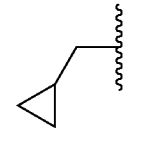 [SMILES: *CC1CC1] | CH$_3$ | H | H | B1, from Int. No. 11 |
| 88 | N-[[2-[(2R,6S)-2,6-dimethyl-4-morpholinyl]-5-(2-methyl-4-pyridinyl)-4-thiazolyl]methyl]-cyclopropaneacetamide | 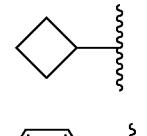 | CH$_3$ | H | H | B1, from Int. No. 11 |
| 89 | N-[[2-[(2R,6S)-2,6-dimethyl-4-morpholinyl]-5-(2-methyl-4-pyridinyl)-4-thiazolyl]methyl]-cyclobutanecarboxamide | 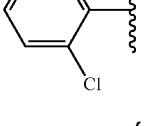 | CH$_3$ | H | H | B2, from Int. No. 11 |
| 90 | 2-chloro-N-[[2-[(2R,6S)-2,6-dimethyl-4-morpholinyl]-5-(2-methyl-4-pyridinyl)-4-thiazolyl]methyl]-benzamide, | 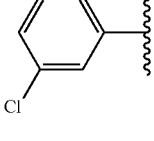 | CH$_3$ | H | H | B2, from Int. No. 11 |
| 91 | 3-chloro-N-[[2-[(2R,6S)-2,6-dimethyl-4-morpholinyl]-5-(2-methyl-4-pyridinyl)-4-thiazolyl]methyl]-benzamide | 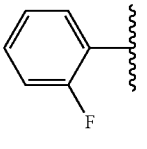 [SMILES: *c1ccccc1F] | CH$_3$ | H | H | B2, from Int. No. 11 |
| 92 | N-[[2-[(2R,6S)-2,6-dimethyl-4-morpholinyl]-5-(2-methyl-4-pyridinyl)-4-thiazolyl]methyl]-2-fluoro-benzamide | 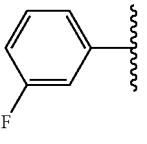 | CH$_3$ | H | H | B2, from Int. No. 11 |
| 93 | N-[[2-[(2R,6S)-2,6-dimethyl-4-morpholinyl]-5-(2-methyl-4-pyridinyl)-4-thiazolyl]methyl]-3-fluoro-benzamide | | CH$_3$ | H | H | B2, from Int. No. 11 |

TABLE 5-continued

Final compounds

| Co. No. | Chemical Name | R1 | R4 | R5 | R6 | Exp. No. |
|---|---|---|---|---|---|---|
| 94 | N-[[2-[(2R,6S)-2,6-dimethyl-4-morpholinyl]-5-(2-methyl-4-pyridinyl)-4-thiazolyl]methyl]-4-fluoro-benzamide | 4-fluorophenyl | CH₃ | H | H | B2, from Int. No. 11 |
| 95 | N-[[2-[(2R,6S)-2,6-dimethyl-4-morpholinyl]-5-(2,5-dimethyl-4-pyridinyl)-4-thiazolyl]methyl]-cyclobutanecarboxamide | cyclobutyl | CH₃ | H | CH₃ | B2, from Int. No. 13 |
| 96 | N-[[2-[(2R,6S)-2,6-dimethyl-4-morpholinyl]-5-(2,5-dimethyl-4-pyridinyl)-4-thiazolyl]methyl]-cyclopentanecarboxamide | cyclopentyl | CH₃ | H | CH₃ | B2, from Int. No. 13 |
| 97 | N-[[2-[(2R,6S)-2,6-dimethyl-4-morpholinyl]-5-(2,5-dimethyl-4-pyridinyl)-4-thiazolyl]methyl]-cyclopropaneacetamide | cyclopropylmethyl | CH₃ | H | CH₃ | B1, from Int. No. 13 |
| 98 | N-[[2-[(2R,6S)-2,6-dimethyl-4-morpholinyl]-5-(2,5-dimethyl-4-pyridinyl)-4-thiazolyl]methyl]-5-methyl-3-isoxazolecarboxamide | 5-methyl-3-isoxazolyl | CH₃ | H | CH₃ | B1, from Int. No. 13 |
| 99 | N-[[2-[(2R,6S)-2,6-dimethyl-4-morpholinyl]-5-(4-pyridinyl)-4-thiazolyl]methyl]-cyclopropaneacetamide | cyclopropylmethyl | H | H | H | B1, from Int. No. 12 |
| 100 | N-[[2-[(2R,6S)-2,6-dimethyl-4-morpholinyl]-5-(4-pyridinyl)-4-thiazolyl]methyl]-5-methyl-3-isoxazolecarboxamide | 5-methyl-3-isoxazolyl | H | H | H | B1, from Int. No. 12 |
| 101 | N-[[2-[(2R,6S)-2,6-dimethyl-4-morpholinyl]-5-(4-pyridinyl)-4-thiazolyl]methyl]-3-methyl-4-isoxazolecarboxamide | 3-methyl-4-isoxazolyl | H | H | H | B1, from Int. No. 12 |
| 102 | N-[[2-[(2R,6S)-2,6-dimethyl-4-morpholinyl]-5-(4-pyridinyl)-4-thiazolyl]methyl]-4-fluoro-2-methyl-benzamide | 4-fluoro-2-methylphenyl | H | H | H | B1, from Int. No. 12 |

TABLE 5-continued

Final compounds

| Co. No. | Chemical Name | R1 | R4 | R5 | R6 | Exp. No. |
|---|---|---|---|---|---|---|
| 103 | N-[[2-[(2R,6S)-2,6-dimethyl-4-morpholinyl]-5-(4-pyridinyl)-4-thiazolyl]methyl]-3-methyl-butanamide | isobutyl | H | H | H | B2, from Int. No. 12 |
| 104 | N-[[5-(2-cyclopropyl-6-methyl-4-pyridinyl)-2-[(2R,6S)-2,6-dimethyl-4-morpholinyl]-4-thiazolyl]methyl]-cyclopropaneacetamide | cyclopropylmethyl | cyclopropyl | CH₃ | H | B1, from Int. No. 14 |
| 105 | N-[[5-(2-cyclopropyl-6-methyl-4-pyridinyl)-2-[(2R,6S)-2,6-dimethyl-4-morpholinyl]-4-thiazolyl]methyl]-5-methyl-3-isoxazolecarboxamide | 5-methyl-isoxazol-3-yl | cyclopropyl | CH₃ | H | B1, from Int. No. 14 |
| 106 | N-[[5-(2-cyclopropyl-6-methyl-4-pyridinyl)-2-[(2R,6S)-2,6-dimethyl-4-morpholinyl]-4-thiazolyl]methyl]-3-methyl-4-isoxazolecarboxamide | 3-methyl-isoxazol-4-yl | cyclopropyl | CH₃ | H | B1, from Int. No. 14 |
| 107 | N-[[5-(2-cyclopropyl-6-methyl-4-pyridinyl)-2-[(2R,6S)-2,6-dimethyl-4-morpholinyl]-4-thiazolyl]methyl]-4-fluoro-2-methyl-benzamide | 4-fluoro-2-methyl-phenyl | cyclopropyl | CH₃ | H | B1, from Int. No. 14 |
| 108 | N-[[5-(2-cyclopropyl-6-methyl-4-pyridinyl)-2-[(2R,6S)-2,6-dimethyl-4-morpholinyl]-4-thiazolyl]methyl]-2-methyl-propanamide | isopropyl | cyclopropyl | CH₃ | H | B2, from Int. No. 14 |
| 109 | N-[[5-(2-cyclopropyl-6-methyl-4-pyridinyl)-2-[(2R,6S)-2,6-dimethyl-4-morpholinyl]-4-thiazolyl]methyl]-cyclopropanecarboxamide | cyclopropyl | cyclopropyl | CH₃ | H | B1, from Int. No. 14 |
| 110 | N-[[5-(2-cyclopropyl-6-methyl-4-pyridinyl)-2-[(2R,6S)-2,6-dimethyl-4-morpholinyl]-4-thiazolyl]methyl]-3-methyl-butanamide | isobutyl | cyclopropyl | CH₃ | H | B2, from Int. No. 14 |

TABLE 5-continued

Final compounds

| Co. No. | Chemical Name | R1 | R4 | R5 | R6 | Exp. No. |
|---|---|---|---|---|---|---|
| 197 | N-[[2-[(2R,6S)-2,6-dimethyl-4-morpholinyl]-5-[2-(trifluoromethyl)-4-pyridinyl]-4-thiazolyl]methyl]-3-methyl-4-isoxazolecarboxamide | (3-methyl-isoxazol-4-yl) | H | $CF_3$ | H | B1, from Int. No. 22 |
| 198 | N-[[2-[(2R,6S)-2,6-dimethyl-4-morpholinyl]-5-[2-(trifluoromethyl)-4-pyridinyl]-4-thiazolyl]methyl]-4-fluoro-2-methyl-benzamide | (4-fluoro-2-methyl-phenyl) | H | $CF_3$ | H | B1, from Int. No. 22 |
| 199 | N-[[2-[(2R,6S)-2,6-dimethyl-4-morpholinyl]-5-[2-(trifluoromethyl)-4-pyridinyl]-4-thiazolyl]methyl]-5-methyl-3-isoxazolecarboxamide | (5-methyl-isoxazol-3-yl) | H | $CF_3$ | H | B2, from Int. No. 22 |
| 200 | N-[[2-[(2R,6S)-2,6-dimethyl-4-morpholinyl]-5-[2-(trifluoromethyl)-4-pyridinyl]-4-thiazolyl]methyl]-cyclopropaneacetamide | (cyclopropylmethyl) | H | $CF_3$ | H | B1, from Int. No. 22 |
| 201 | N-[[2-[(2R,6S)-2,6-dimethyl-4-morpholinyl]-5-[2-(trifluoromethyl)-4-pyridinyl]-4-thiazolyl]methyl]-2-methyl-propanamide | (isopropyl) | H | $CF_3$ | H | B2, from Int. No. 22 |

TABLE 6

Final compounds

| Co. No. | Chemical Name | R1 | Exp. No. |
|---|---|---|---|
| 111 | 5-methyl-N-[[2-(4-morpholinyl)-5-(4-pyridinyl)-4-thiazolyl]methyl]-3-isoxazolecarboxamide | (5-methyl-isoxazol-3-yl) | B1, from Int. No. 17 |

TABLE 6-continued

Final compounds

| Co. No. | Chemical Name | R1 | Exp. No. |
|---|---|---|---|
| 112 | N-[[2-(4-morpholinyl)-5-(4-pyridinyl)-4-thiazolyl]methyl]-cyclopropaneacetamide | cyclopropylmethyl | B1, from Int. No. 17 |
| 113 | 4-fluoro-2-methyl-N-[[2-(4-morpholinyl)-5-(4-pyridinyl)-4-thiazolyl]methyl]-benzamide | 4-fluoro-2-methylphenyl | B1, from Int. No. 17 |
| 114 | 3-methyl-N-[[2-(4-morpholinyl)-5-(4-pyridinyl)-4-thiazolyl]methyl]-4-isoxazolecarboxamide | 3-methyl-4-isoxazolyl | B1, from Int. No. 17 |
| 115 | 2-methyl-N-[[2-(4-morpholinyl)-5-(4-pyridinyl)-4-thiazolyl]methyl]-propanamide | isopropyl | B2, from Int. No. 17 |
| 116 | N-[[2-(4-morpholinyl)-5-(4-pyridinyl)-4-thiazolyl]methyl]-cyclopropanecarboxamide | cyclopropyl | B1, from Int. No. 17 |

TABLE 7

Final compounds

| Co. No. | Chemical name | R1 | Exp. No. |
|---|---|---|---|
| 117 | N-[[2-[(2R,6S)-2,6-dimethyl-4-morpholinyl]-5-(6-methyl-3-pyridinyl)-4-thiazolyl]methyl]-3-methyl-4-isoxazolecarboxamide | 3-methyl-4-isoxazolyl | B1, from Int. No. 9 |

TABLE 7-continued

Final compounds

| Co. No. | Chemical name | R1 | Exp. No. |
|---|---|---|---|
| 118 | N-[[2-[(2R,6S)-2,6-dimethyl-4-morpholinyl]-5-(6-methyl-3-pyridinyl)-4-thiazolyl]methyl]-5-methyl-3-isoxazolecarboxamide | 5-methyl-isoxazol-3-yl | B1, from Int. No. 9 |
| 119 | N-[[2-[(2R,6S)-2,6-dimethyl-4-morpholinyl]-5-(6-methyl-3-pyridinyl)-4-thiazolyl]methyl]-cyclopropaneacetamide | cyclopropylmethyl | B1, from Int. No. 9 |
| 120 | N-[[2-[(2R,6S)-2,6-dimethyl-4-morpholinyl]-5-(6-methyl-3-pyridinyl)-4-thiazolyl]methyl]-cyclobutanecarboxamide | cyclobutyl | B2, from Int. No. 9 |
| 121 | 2-chloro-N-[[2-[(2R,6S)-2,6-dimethyl-4-morpholinyl]-5-(6-methyl-3-pyridinyl)-4-thiazolyl]methyl]-benzamide, | 2-chlorophenyl | B2, from Int. No. 9 |
| 122 | 3-chloro-N-[[2-[(2R,6S)-2,6-dimethyl-4-morpholinyl]-5-(6-methyl-3-pyridinyl)-4-thiazolyl]methyl]-benzamide, | 3-chlorophenyl | B2, from Int. No. 9 |
| 123 | 4-chloro-N-[[2-[(2R,6S)-2,6-dimethyl-4-morpholinyl]-5-(6-methyl-3-pyridinyl)-4-thiazolyl]methyl]-benzamide | 4-chlorophenyl | B2, from Int. No. 9 |
| 124 | N-[[2-[(2R,6S)-2,6-dimethyl-4-morpholinyl]-5-(6-methyl-3-pyridinyl)-4-thiazolyl]methyl]-2-fluoro-benzamide | 2-fluorophenyl | B2, from Int. No. 9 |
| 125 | N-[[2-[(2R,6S)-2,6-dimethyl-4-morpholinyl]-5-(6-methyl-3-pyridinyl)-4-thiazolyl]methyl]-3-fluoro-benzamide | 3-fluorophenyl | B2, from Int. No. 9 |
| 126 | N-[[2-[(2R,6S)-2,6-dimethyl-4-morpholinyl]-5-(6-methyl-3-pyridinyl)-4-thiazolyl]methyl]-4-fluoro-benzamide | 4-fluorophenyl | B2, from Int. No. 9 |

Analytical Part
LCMS
LCMS General Procedure A

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS General Procedure B

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS—Method 1

In addition to the general procedure A: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used.

Cone voltage was 10 V for positive ionization mode and 20 V for negative ionization mode.

LCMS—Method 2

In addition to the general procedure A: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used.

Cone voltage was 30 V for positive ionization mode and 30 V for negative ionization mode.

LCMS—Method 3

In addition to the general procedure A: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used.

Cone voltage was 10 V for positive ionization mode and 20 V for negative ionization mode.

LCMS—Method 4

In addition to the general procedure B: Column heater was set at 45° C. Reversed phase HPLC was carried out on an Atlantis C18 column (3.5 μm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 9 minutes and hold these conditions for 3 minutes. An injection volume of 10 μl was used.

Cone voltage was 10 V for positive ionization mode and 20 V for negative ionization mode.

LCMS—Method 5

In addition to the general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Method 6

In addition to general procedure B: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A, 99% B in 0.5 minute and keep these conditions for 1 minute. An injection volume of 10 μl was used. Cone voltage was 10 V for positive ionization mode and 20 V for negative ionization mode.

Melting Points

For a number of compounds, melting points were determined with a DSC823e from Mettler-Toledo. Melting points were measured with a temperature gradient of 30° C./minute. Values are peak values.

TABLE 8

Analytical data - Retention time ($R_t$ in minutes), $(MH)^+$ peak, LCMS method and melting points ("m.p." is defined as melting point; "—" means no value).

| Co. Nr. | Rt | (MH)+ | LCMS Method | m.p. (° C.) |
|---|---|---|---|---|
| 1 | 0.95 | 415 | 1 | 174° C. |
| 2 | 0.97 | 415 | 1 | — |
| 3 | 0.97 | 442 | 1 | 208° C. |
| 4 | 1.02 | 442 | 1 | 184° C. |
| 5 | 1.06 | 471 | 1 | — |
| 6 | 1.09 | 455 | 1 | — |
| 7 | 1.09 | 455 | 1 | — |
| 8 | 1.08 | 455 | 1 | — |
| 9 | 1.16 | 471 | 1 | — |
| 10 | 1.19 | 505 | 1 | — |
| 11 | 1.23 | 521 | 1 | — |
| 12 | 1.02 | 462 | 1 | — |
| 13 | 1.14 | 473 | 1 | — |
| 14 | 1.17 | 491 | 1 | — |
| 15 | 1.15 | 473 | 1 | — |
| 16 | 1.08 | 429 | 1 | — |
| 17 | 0.86 | 452 | 1 | — |
| 18 | 1.01 | 442 | 1 | 141° C. |

TABLE 8-continued

Analytical data - Retention time ($R_t$ in minutes), $(MH)^+$ peak, LCMS method and melting points ("m.p." is defined as melting point; "—" means no value).

| Co. Nr. | Rt | (MH)+ | LCMS Method | m.p. (° C.) |
|---|---|---|---|---|
| 19 | 1.20 | 472 | 1 | — |
| 20 | 1.18 | 510 | 1 | — |
| 21 | 1.19 | 465 | 1 | — |
| 22 | 1.22 | 486 | 1 | — |
| 23 | 1.23 | 505 | 1 | — |
| 24 | 1.14 | 469 | 1 | — |
| 25 | 1.01 | 456 | 1 | — |
| 26 | 1.18 | 506 | 1 | — |
| 27 | 1.08 | 437 | 1 | — |
| 28 | 0.91 | 431 | 1 | — |
| 29 | 1.06 | 472 | 1 | — |
| 30 | 1.12 | 467 | 1 | — |
| 31 | 1.05 | 442 | 1 | — |
| 32 | 1.08 | 473 | 1 | — |
| 33 | 1.17 | 523 | 1 | — |
| 34 | 0.99 | 415 | 1 | — |
| 35 | 1.21 | 505 | 1 | 185° C. |
| 36 | 1.10 | 473 | 1 | 189° C. |
| 37 | 0.88 | 405 | 1 | 150° C. |
| 38 | 1.10 | 487 | 1 | 187° C. |
| 39 | 0.88 | 389 | 1 | 176° C. |
| 40 | 0.94 | 403 | 1 | — |
| 41 | 0.94 | 403 | 1 | 155° C. |
| 42 | 1.01 | 417 | 1 | 184° C. |
| 43 | 1.18 | 457 | 1 | 197° C. |
| 44 | 1.14 | 505 | 1 | 180° C. |
| 45 | 1.16 | 517 | 1 | 175° C. |
| 46 | 1.20 | 517 | 1 | 185° C. |
| 47 | 1.02 | 417 | 1 | — |
| 48 | 0.90 | 401 | 1 | — |
| 49 | 1.06 | 429 | 1 | 153° C. |
| 50 | 1.04 | 429 | 1 | 168° C. |
| 51 | 1.28 | 431 | 1 | — |
| 52 | 0.95 | 444 | 2 | — |
| 53 | 0.85 | 419 | 1 | — |
| 54 | 1.17 | 497 | 2 | — |
| 55 | 0.92 | 415 | 2 | — |
| 56 | 1.05 | 469 | 2 | — |
| 57 | 0.93 | 415 | 2 | — |
| 58 | 1.09 | 472 | 2 | 184° C. |
| 59 | 0.98 | 442 | 2 | 166° C. |
| 60 | 0.91 | 375 | 1 | — |
| 61 | 0.87 | 403 | 1 | — |
| 62 | 0.75 | 414 | 1 | — |
| 63 | 0.82 | 414 | 1 | 197° C. |
| 64 | 0.79 | 387 | 1 | 188° C. |
| 65 | 0.80 | 387 | 1 | 188° C. |
| 66 | 0.89 | 427 | 1 | 210° C. |
| 67 | 0.76 | 375 | 1 | 178° C. |
| 68 | 0.88 | 442 | 1 | — |
| 69 | 0.84 | 428 | 1 | — |
| 70 | 1.03 | 455 | 1 | 185° C. |
| 71 | 0.86 | 389 | 1 | 188° C. |
| 72 | 0.88 | 428 | 1 | 138° C. |
| 73 | 0.85 | 428 | 2 | — |
| 74 | 0.92 | 428 | 2 | 167° C. |
| 75 | 0.87 | 401 | 2 | 170° C. |
| 76 | 0.85 | 389 | 2 | 189° C. |
| 77 | 0.99 | 455 | 2 | 188° C. |
| 78 | 0.90 | 401 | 1 | 169° C. |
| 79 | 0.90 | 428 | 1 | 166° C. |
| 80 | 0.92 | 441 | 2 | 221° C. |
| 81 | 1.11 | 458 | 3 | — |
| 82 | 1.19 | 458 | 3 | 203° C. |
| 83 | 1.12 | 431 | 3 | 171° C. |
| 84 | 1.14 | 431 | 3 | 171° C. |
| 85 | 1.26 | 471 | 3 | 172° C. |
| 86 | 0.91 | 428 | 3 | — |
| 87 | 0.98 | 428 | 3 | 177° C. |
| 88 | 0.93 | 401 | 3 | 177° C. |
| 89 | 0.94 | 401 | 3 | — |
| 90 | 1.03 | 457 | 3 | 155° C. |
| 91 | 1.09 | 457 | 3 | — |
| 92 | 1.06 | 441 | 3 | — |
| 93 | 1.02 | 441 | 3 | 153° C. |
| 94 | 1.01 | 441 | 3 | 225° C. |
| 95 | 6.11 | 415 | 4 | — |
| 96 | 6.54 | 429 | 4 | 173° C. |
| 97 | 6.09 | 415 | 4 | 138° C. |
| 98 | 6.17 | 442 | 4 | 155° C. |
| 99 | 0.87 | 387 | 2 | 178° C. |
| 100 | 0.92 | 414 | 2 | 182° C. |
| 101 | 0.84 | 414 | 2 | — |
| 102 | 0.99 | 441 | 2 | 161° C. |
| 103 | 0.91 | 389 | 2 | 173° C. |
| 104 | 1.26 | 441 | 1 | — |
| 105 | 1.29 | 468 | 1 | — |
| 106 | 1.24 | 468 | 1 | — |
| 107 | 1.41 | 495 | 1 | — |
| 108 | 1.25 | 429 | 1 | — |
| 109 | 1.22 | 427 | 1 | — |
| 110 | 1.34 | 443 | 1 | — |
| 111 | 0.76 | 386 | 2 | 191° C. |
| 112 | 0.71 | 359 | 2 | 135° C. |
| 113 | 0.99 | 413 | 1 | 191° C. |
| 114 | 0.76 | 386 | 1 | 234° C. |
| 115 | 0.77 | 347 | 1 | — |
| 116 | 0.73 | 345 | 1 | 189° C. |
| 117 | 0.92 | 428 | 3 | 129° C. |
| 118 | 0.99 | 428 | 3 | 148° C. |
| 119 | 0.94 | 401 | 3 | 139° C. |
| 120 | 0.95 | 401 | 3 | 139° C. |
| 121 | 1.04 | 457 | 3 | 152° C. |
| 122 | 1.10 | 457 | 3 | 167° C. |
| 123 | 1.09 | 457 | 3 | 208° C. |
| 124 | 1.06 | 441 | 3 | — |
| 125 | 1.03 | 441 | 3 | 147° C. |
| 126 | 1.02 | 441 | 3 | 195° C. |
| 127 | 1.12 | 468 | 2 | — |
| 128 | 0.99 | 457 | 1 | — |
| 129 | 1.12 | 497 | 2 | — |
| 130 | 1.12 | 478 | 2 | — |
| 131 | 0.96 | 455 | 2 | — |
| 133 | 1.03 | 469 | 1 | 156° C. |
| 134 | 1.06 | 456 | 2 | — |
| 135 | 1.18 | 470 | 2 | — |
| 136 | 0.95 | 455 | 2 | — |
| 138 | 0.94 | 439 | 2 | — |
| 139 | 1.21 | 497 | 2 | — |
| 140 | 1.14 | 468 | 2 | — |
| 141 | 0.94 | 427 | 2 | — |
| 142 | 0.92 | 441 | 2 | — |
| 143 | 1.25 | 484 | 2 | — |
| 144 | — | — | — | — |
| 145 | 1.02 | 471 | 1 | — |
| 146 | 1.09 | 455 | 2 | 131° C. |
| 147 | 1.07 | 441 | 2 | 149° C. |
| 148 | 1.01 | 442 | 2 | — |
| 149 | 0.92 | 428 | 2 | 164° C. |
| 150 | 1.11 | 457 | 2 | 184° C. |
| 151 | 1.03 | 441 | 2 | — |
| 152 | 0.90 | 442 | 2 | — |
| 153 | 0.92 | 458 | 2 | — |
| 154 | 0.92 | 473 | 2 | — |
| 155 | 0.96 | 459 | 1 | — |
| 156 | 5.35 | 415 | 5 | 135° C. |
| 157 | 5.89 | 469 | 5 | 197° C. |
| 158 | 1.05 | 488 | 2 | — |
| 159 | 0.94 | 456 | 2 | 193° C. |
| 160 | 0.87 | 455 | 2 | 169° C. |
| 161 | 1.00 | 442 | 2 | 201° C. |
| 162 | — | — | — | — |
| 163 | 1.14 | 510 | 2 | 176° C. |
| 164 | 1.05 | 471 | 1 | 200° C. |
| 165 | 1.10 | 520 | 2 | — |
| 166 | 0.93 | 470 | 2 | — |

TABLE 8-continued

Analytical data - Retention time ($R_t$ in minutes), $(MH)^+$ peak, LCMS method and melting points ("m.p." is defined as melting point; "—" means no value).

| Co. Nr. | Rt | (MH)+ | LCMS Method | m.p. (° C.) |
|---|---|---|---|---|
| 167 | 0.91 | 456 | 2 | — |
| 168 | 0.98 | 443 | 2 | — |
| 169 | 0.87 | 455 | 2 | — |
| 170 | 0.86 | 400 | 2 | — |
| 171 | 5.61 | 456 | 6 | 192° C. |
| 172 | 5.81 | 455 | 6 | 165° C. |
| 173 | 1.15 | 455 | 2 | — |
| 174 | 0.82 | 442 | 1 | 145° C. |
| 175 | 1.06 | 473 | 2 | — |
| 176 | 0.71 | 417 | 1 | — |
| 177 | 0.86 | 429 | 1 | — |
| 178 | 0.89 | 458 | 1 | 180° C. |
| 179 | 1.04 | 429 | 2 | — |
| 180 | 0.97 | 428 | 2 | 179° C. |
| 181 | 5.68 | 442 | 5 | — |
| 182 | 5.36 | 442 | 5 | — |
| 183 | 5.36 | 403 | 5 | — |
| 184 | 1.00 | 455 | 2 | 156° C. |
| 185 | 0.85 | 428 | 2 | — |
| 186 | 0.84 | 428 | 1 | — |
| 187 | 0.87 | 401 | 2 | 138° C. |
| 188 | 0.85 | 389 | 2 | — |
| 189 | 0.91 | 403 | 2 | 151° C. |
| 190 | 1.01 | 455 | 2 | 168° C. |
| 191 | 1.00 | 455 | 2 | 182° C. |
| 192 | 1.00 | 455 | 2 | 183° C. |
| 193 | 1.12 | 509 | 2 | — |
| 194 | 1.00 | 443 | 2 | 189° C. |
| 195 | 1.06 | 482 | 2 | 170° C. |
| 196 | 0.99 | 482 | 2 | 178° C. |
| 197 | 1.23 | 482 | 1 | 205° C. |
| 198 | 1.22 | 509 | 2 | — |
| 199 | 1.16 | 482 | 2 | 228° C. |
| 200 | 1.11 | 455 | 2 | 198° C. |
| 201 | 1.10 | 443 | 2 | 216° C. |
| 202 | 1.09 | 469 | 2 | — |
| 203 | 1.07 | 469 | 2 | — |
| 204 | 1.07 | 469 | 2 | — |
| 205 | 0.97 | 469 | 1 | 148° C. |
| 206 | 1.02 | 469 | 1 | 150° C. |
| 207 | 4.86 | 401 | 6 | 179° C. |
| 208 | 5.50 | 467 | 6 | 194° C. |
| 209 | 5.03 | 413 | 6 | 161° C. |
| 210 | 5.25 | 440 | 6 | 206° C. |
| 211 | 5.02 | 440 | 5 | 94° C. |

Optical Rotation (OR)

The optical rotation was measured using a Perkin Elmer 341 polarimeter. $[\alpha]_D^{20}$ indicates the optical rotation measured with light at the wavelength ($\lambda$) of 589 nm, at a temperature of 20° C., in MeOH. The cell pathlength is 1 dm. Behind the actual value the concentration which was used to measure the optical rotation is mentioned.
Compound 206: +21.3° (0.3428 w/v %)
Compound 133: −21.83° (0.3756 w/v %)
Compound 203: +21.35° (0.2248 w/v %)
Compound 204: −21.67° (0.1846 w/v %)
NMR (Nuclear Magnetic Resonance)

For a number of compounds, $^1$H NMR spectra were recorded on a Bruker DPX-360, on a Bruker DPX-400 or on a Bruker Avance 600 spectrometer with standard pulse sequences, operating at 360 MHz, 400 MHz and 600 MHz respectively, using CHLOROFORM-d (deuterated chloroform, $CDCl_3$) or DMSO-$d_6$ (deuterated DMSO, dimethyl-d6 sulfoxide) as solvents. Chemical shifts (δ) are reported in parts per million (ppm) relative to tetramethylsilane (TMS), which was used as internal standard.

Compound 133: $^1$H NMR (360 MHz, DMSO-$d_6$) δ ppm 0.06-0.17 (m, 2H), 0.35-0.44 (m, 2H), 0.89-1.00 (m, 1H), 1.24 (d, J=6.2 Hz, 3H), 2.01 (d, J=7.0 Hz, 2H), 2.42 (s, 6H), 3.18 (dd, J=12.6, 7.1 Hz, 1H), 3.65 (dd, J=13.2, 3.3 Hz, 1H), 3.68 (dd, J=13.5, 5.5 Hz, 1H), 3.78 (dd, J=13.5, 4.4 Hz, 1H), 4.15-4.24 (m, 1H), 4.27 (d, J=5.5 Hz, 2H), 4.52-4.81 (m, 1H), 7.08 (s, 2H), 8.13 (t, J=5.3 Hz, 1H).

Compound 184: $^1$H NMR (400 MHz, DMSO-$d_6$) δ ppm 1.26 (d, J=6.7 Hz, 3H), 2.35 (s, 3H), 2.43 (s, 6H), 3.28-3.38 (m, 1H), 3.47-3.57 (m, 2H), 3.63 (dd, J=11.7, 2.8 Hz, 1H), 3.70 (d, J=11.3 Hz, 1H), 3.89-3.95 (m, 1H), 3.99 (qd, J=6.7, 2.8 Hz, 1H), 4.45 (d, J=5.5 Hz, 2H), 7.03 (td, J=8.6, 2.7 Hz, 1H), 7.06-7.11 (m, 3H), 7.32 (dd, J=8.5, 6.1 Hz, 1H), 8.61 (t, J=5.4 Hz, 1H).

Compound 185: $^1$H NMR (360 MHz, DMSO-$d_6$) δ ppm 1.25 (d, J=6.7 Hz, 3H), 2.37 (s, 3H), 2.41 (s, 6H), 3.27-3.36 (m, 1H), 3.45-3.59 (m, 2H), 3.63 (dd, J=11.3, 2.9 Hz, 1H), 3.70 (d, J=11.3 Hz, 1H), 3.88-3.99 (m, 2H), 4.37-4.48 (m, 2H), 7.08 (s, 2H), 8.72 (t, J=5.3 Hz, 1H), 9.25 (s, 1H).

Compound 190: $^1$H NMR (360 MHz, CHLOROFORM-d) δ ppm 0.14-0.30 (m, 2H), 0.53-0.68 (m, 2H), 0.91-1.07 (m, 1H), 2.21 (d, J=7.3 Hz, 2H), 2.56 (s, 6H), 3.20 (t, J=11.5 Hz, 1H), 3.32 (td, J=12.1, 3.3 Hz, 1H), 3.70 (d, J=13.2 Hz, 1H), 3.81 (t, J=11.7 Hz, 1H), 3.96-4.21 (m, 3H), 4.51 (d, J=4.0 Hz, 2H), 6.82 (br. s., 1H), 6.98 (s, 2H).

Compound 191: $^1$H NMR (600 MHz, DMSO-$d_6$) δ ppm 0.09-0.13 (m, 2H), 0.37-0.42 (m, 2H), 0.90-0.98 (m, 1H), 2.01 (d, J=7.1 Hz, 2H), 2.43 (s, 6H), 3.18 (dd, J=12.5, 10.6 Hz, 1H), 3.28 (ddd, J=12.5, 11.7, 3.5 Hz, 1H), 3.66 (d, J=12.7 Hz, 1H), 3.77 (td, J=11.6, 2.9 Hz, 1H), 4.06-4.10 (m, 1H), 4.08-4.12 (m, 1H), 4.28 (d, J=5.3 Hz, 2H), 4.39-4.48 (m, 1H), 7.09 (s, 2H), 8.09 (t, J=5.3 Hz, 1H).

Compound 192: $^1$H NMR (600 MHz, DMSO-$d_6$) δ ppm 0.09-0.13 (m, 2H), 0.37-0.42 (m, 2H), 0.90-0.98 (m, 1H), 2.01 (d, J=7.1 Hz, 2H), 2.43 (s, 6H), 3.18 (dd, J=12.5, 10.6 Hz, 1H), 3.28 (ddd, J=12.5, 11.7, 3.5 Hz, 1H), 3.66 (d, J=12.7 Hz, 1H), 3.77 (td, J=11.6, 2.9 Hz, 1H), 4.06-4.10 (m, 1H), 4.08-4.12 (m, 1H), 4.28 (d, J=5.3 Hz, 2H), 4.39-4.48 (m, 1H), 7.09 (s, 2H), 8.09 (t, J=5.3 Hz, 1H).

Compound 193: $^1$H NMR (360 MHz, CHLOROFORM-d) δ ppm 2.49 (s, 3H), 2.56 (s, 6H), 3.19 (dd, J=12.1, 10.6 Hz, 1H), 3.31 (td, J=12.3, 3.3 Hz, 1H), 3.81 (td, J=11.7, 2.9 Hz, 1H), 3.71 (d, J=13.2 Hz, 1H), 3.98-4.21 (m, 3H), 4.66 (d, J=4.8 Hz, 2H), 6.52 (br. s., 1H), 6.85-6.98 (m, 2H), 7.00 (s, 2H), 7.41 (dd, J=8.4, 5.9 Hz, 1H).

Compound 194: $^1$H NMR (360 MHz, CHLOROFORM-d) δ ppm 1.18 (d, J=7.0 Hz, 6H), 2.42 (spt, J=6.8 Hz, 1H), 2.54 (s, 6H), 3.20 (dd, J=12.4, 10.6 Hz, 1H), 3.31 (td, J=12.3, 3.7 Hz, 1H), 3.81 (td, J=11.6, 2.7 Hz, 1H), 3.72 (d, J=13.5 Hz, 1H), 4.01-4.20 (m, 3H), 4.48 (d, J=5.1 Hz, 2H), 6.25 (br. s., 1H), 6.94 (s, 2H).

Compound 195: $^1$H NMR (360 MHz, CHLOROFORM-d) δ ppm 2.48 (s, 3H), 2.55 (s, 6H), 3.21 (dd, J=13.1, 11.2 Hz, 1H), 3.25-3.35 (m, 1H), 3.66-3.86 (m, 2H), 3.97-4.11 (m, 2H), 4.11-4.26 (m, 1H), 4.63 (d, J=5.1 Hz, 2H), 6.46 (s, 1H), 6.98 (s, 2H), 7.47 (t, J=4.8 Hz, 1H).

Compound 196: $^1$H NMR (360 MHz, CHLOROFORM-d) δ ppm 2.54 (s, 3H), 2.55 (s, 6H), 3.21 (t, J=11.5 Hz, 1H), 3.33 (td, J=12.3, 3.5 Hz, 1H), 3.71 (d, J=12.4 Hz, 1H), 3.82 (td, J=11.7, 2.6 Hz, 1H), 4.01-4.14 (m, 2H), 4.18 (dd, J=11.5, 2.7 Hz, 1H), 4.62 (d, J=4.4 Hz, 2H), 6.72 (br. s., 1H), 6.96 (s, 2H), 8.73 (s, 1H).

Compound 203: $^1$H NMR (360 MHz, DMSO-$d_6$) δ ppm 0.06-0.13 (m, 2H), 0.35-0.42 (m, 2H), 0.89-1.00 (m, 1H), 1.23 (d, J=6.2 Hz, 3H), 2.01 (d, J=7.0 Hz, 2H), 2.42 (s, 6H), 2.90 (d, J=12.4, 11.0 Hz, 1H), 3.08 (t, J=11.7 Hz, 1H), 3.75 (d, J=12.5 Hz, 1H), 3.84-3.93 (m, 1H), 4.09 (d, J=12.2 Hz, 1H), 4.27 (d, J=5.1 Hz, 2H), 4.44-4.54 (m, 1H), 7.09 (s, 2H), 8.14 (t, J=5.3 Hz, 1H).

Compound 204: $^1$H NMR (360 MHz, DMSO-d$_6$) δ ppm 0.06-0.13 (m, 2H), 0.35-0.42 (m, 2H), 0.89-1.00 (m, 1H), 1.23 (d, J=6.2 Hz, 3H), 2.01 (d, J=7.0 Hz, 2H), 2.42 (s, 6H), 2.90 (dd, J=12.4, 11.0 Hz, 1H), 3.08 (t, J=11.7 Hz, 1H), 3.75 (d, J=12.5 Hz, 1H), 3.84-3.93 (m, 1H), 4.09 (d, J=12.2 Hz, 1H), 4.27 (d, J=5.1 Hz, 2H), 4.44-4.54 (m, 1H), 7.09 (s, 2H), 8.14 (t, J=5.3 Hz, 1H).

Compound 205: $^1$H NMR (360 MHz, DMSO-d$_6$) δ ppm 0.06-0.17 (m, 2H), 0.35-0.44 (m, 2H), 0.89-1.00 (m, 1H), 1.24 (d, J=6.2 Hz, 3H), 2.01 (d, J=7.0 Hz, 2H), 2.42 (s, 6H), 3.18 (dd, J=12.6, 7.1 Hz, 1H), 3.65 (dd, J=13.2, 3.3 Hz, 1H), 3.68 (dd, J=13.5, 5.5 Hz, 1H), 3.78 (dd, J=13.5, 4.4 Hz, 1H), 4.15-4.24 (m, 1H), 4.27 (d, J=5.5 Hz, 2H), 4.52-4.81 (m, 1H), 7.08 (s, 2H), 8.13 (t, J=5.3 Hz, 1H).

Compound 206: $^1$H NMR (360 MHz, DMSO-d$_6$) δ ppm 0.06-0.17 (m, 2H), 0.35-0.44 (m, 2H), 0.89-1.00 (m, 1H), 1.24 (d, J=6.2 Hz, 3H), 2.01 (d, J=7.0 Hz, 2H), 2.42 (s, 6H), 3.18 (dd, J=12.6, 7.1 Hz, 1H), 3.65 (dd, J=13.2, 3.3 Hz, 1H), 3.68 (dd, J=13.5, 5.5 Hz, 1H), 3.78 (dd, J=13.5, 4.4 Hz, 1H), 4.15-4.24 (m, 1H), 4.27 (d, J=5.5 Hz, 2H), 4.52-4.81 (m, 1H), 7.08 (s, 2H), 8.13 (t, J=5.3 Hz, 1H).

D. Pharmacological Examples

Example D.1

Ca$^{2+}$ Flux Imaging (FDSS) (Protocol B)

Materials
a) Assay Buffer
   Hanks buffered saline solution (HBSS, Invitrogen, Belgium), supplemented with 10 mM HEPES (Invitrogen, Belgium), CaCl$_2$ to a final concentration of 5 mM, 0.1% Bovine serum albumin (Sigma-Aldrich NV, Belgium).
b) Calcium-Sensitive Dye—Fluo-4AM
   Fluo-4AM (Molecular Probes, USA) was dissolved in DMSO containing 10% Pluronic acid (Molecular Probes, USA) to give a stock solution which was diluted in assay buffer supplemented with 5 mM probenicid (Sigma, Aldrich NV, Belgium) to give a final concentration of 2 μM.
c) 384-Well Plates
   Black-sided, transparent bottomed 384 well plates coated with poly-D-lysine, PDL pre-coated (Corning, Incorporated, USA)
d) Calcium Flux Measurement
   A Functional drug screening system (FDSS, Hamamatsu) was used to measure intracellular free-calcium flux signals.

Method

Monolayers of human alpha 7-wt nAChR-expressing cells were grown in black-sided, transparent bottomed 384 well plates coated with PDL for 24 hours prior to loading with a fluorescent calcium indicator, fluo-4AM for up to 120 minutes.

PAM activity was detected in real time by applying the compounds to be tested to the loaded cells along with an alpha 7 nicotinic receptor agonist during constant monitoring of cellular fluorescence in a FDSS. Compounds giving peak fluorescent responses greater than the response due to agonist alone, were considered to be alpha 7 nAChR PAMs. The alpha 7 nicotinic receptor agonist was choline, applied at a sub-maximal concentration of 100 μM. In a further setting of the present invention the compounds were applied prior to the alpha 7 nicotinic receptor agonist, in a particular 10 minutes prior to the agonist.

A control response to choline was calculated on each plate from the difference in peak in fluorescence in wells receiving either choline or assay buffer alone. Compounds of the present invention were tested at a concentration range from 0.01 μM to 30 μM. Compounds were considered to have an interesting activity when they potentiated the choline signal at least with 200% when tested at a concentration of 30 μM (the efficacy of 100 μM choline was defined as 100% in the absence of a PAM). An EC$_{50}$ (or pEC$_{50}$) was determined as a concentration relating to half the maximal effect, when a clear sigmoidal curve with top plateau was obtained. The EC$_{50}$ (or pEC$_{50}$) was defined as lower than maximal concentration in case the compound activity did not reach a top plateau at maximal concentration (indicated in table 9 as "<5")

The compounds also have a potentiating effect on the response to choline when measured by whole-cell patch clamp electrophysiology in GH4C1 cells stably over-expressing the human wild-type alpha 7 receptor.

Example D.2

Patch-Clamp Current Recording

Patch-clamp recording from mammalian cells has provided a powerful means of assessing the function of membrane-bound proteins thought to be subunits of ligand-gated ion channels. Activation of such proteins by endogenous or exogenous ligands cause opening of a pore associated with the receptor through which ions flow down their electrochemical gradient. In the case of the human alpha 7-wt nAChR-expressing GH4C1 recombinant cell line the preferential permeability to calcium of this receptor means that calcium flows into the cell upon activation by ACh, choline and other nicotinic ligands giving rise to a calcium current. Since this receptor rapidly desensitizes in the presence of agonist it is important that an application system is used which is capable of very rapid switching of solutions (<100 ms) to prevent partial or full desensitisation of receptor responses coincident with the time of agonist application. Consequently, a second convenient technique to assess the enhancement of nicotinic efficacy is a patch-clamp recording from human alpha 7-wt nAChR-expressing GH4C1 cells coupled with a rapid-application system.

Materials
a) Assay Buffers
   The external recording solution consisted of 152 mM NaCl, 5 mM KCl, 1 mM MgCl$_2$, 1 mM Calcium, 10 mM HEPES; pH 7.3. The internal recording solution consisted of 140 mM CsCl, 10 mM HEPES, 10 mM EGTA, 1 mM MgCl$_2$, pH 7.3.
b) Patch-clamp recording was carried out using a Patch-clamp amplifier (Multiclamp 700A, Axon Instruments, CA, USA). Human alpha 7-wt nAChR-expressing GH4C1 cells were patch-clamped in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1 GΩ and series resistance <15 MΩ with at least 60% series resistance compensation. Membrane potential was clamped at −70 mV.
c) Agonists
   ACh, choline, were purchased from Sigma-Aldrich NV, Belgium.
d) Compound Application
   A 16-channel Dynflow DF-16 microfluidics system (Cellectricon, Sweden) for rapid switching of solutions (switching resolution time <100 ms) was used to apply control, agonist and PAM compounds to human alpha 7-wt nAChR-expressing GH4C1 cells.

Method

Human alpha 7-wt nAChR-expressing GH4C1 cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (12 µl/min) of external recording solution. PAM activity was detected in real time by pre-applying the compounds to the loaded cells followed by an alpha 7 nicotinic receptor agonist during constant monitoring of cellular membrane current. Compounds giving current responses greater than the response due to agonist alone, were considered to be alpha 7 nAChR PAM's. The alpha 7 nicotinic receptor was activated by a non-selective nicotinic agonist, choline applied at a sub-maximal concentration of 1 mM. In a further setting of the present invention the compounds were applied prior to the alpha 7 nicotinic receptor agonist, 30 seconds prior to the agonist or 5 seconds prior to the agonist. A control response was calculated from the area under the curve of the current elicited in each cell to the application of submaximal choline for 250 ms. Area under the curve is the integration of net current over time and is a common representation of the total ion flux through the channel. Increases in agonist efficacy elicited by a positive allosteric modulator were calculated as percent potentiation of "area under curve" (AUC) of the agonist response. Potentiation greater than control AUC caused by compounds of the invention indicates that they are expected to have useful therapeutic activity. $EC_{50}$ values (potency), maximal effect (% efficacy), and Hill slopes were estimated by fitting the data to the logistic equation using GraphPad Prism (GraphPad Software, Inc., San Diego, Calif.).

TABLE 9

Potency ($pEC_{50}$) and % efficacy for a number of compounds.

| Co. Nr. | a7-PAM-G_[33]_pEC50 pEC50 | a7-PAM-G_[33]_Eff_Curve_FI % Efficacy | PAM_Type PAM type |
|---|---|---|---|
| 1 | 6.73 | 796 | 2 |
| 2 | 7.17 | 1337 | 2 |
| 3 | 6.09 | 1555 | 1 |
| 4 | 5.85 | 927 | 2 |
| 5 | 6.87 | 568 | 2 |
| 6 | — | 313 | — |
| 7 | 6.50 | 723 | 2 |
| 8 | 6.34 | 452 | 2 |
| 9 | 6.62 | 566 | 2 |
| 10 | 7.08 | 630 | 2 |
| 11 | 6.09 | 703 | 2 |
| 12 | 6.26 | 595 | 2 |
| 13 | 6.54 | 593 | 2 |
| 14 | 6.47 | 787 | 2 |
| 15 | 6.77 | 411 | 2 |
| 16 | 7.65 | 651 | — |
| 17 | 6.00 | 499 | 2 |
| 18 | 6.42 | 815 | 2 |
| 19 | 7.00 | 378 | 2 |
| 20 | 5.76 | 253 | — |
| 21 | 7.14 | 572 | — |
| 22 | 7.70 | 484 | 2 |
| 23 | 6.64 | 594 | 2 |
| 24 | 7.76 | 526 | 2 |
| 25 | 6.09 | 235 | 0 |
| 26 | 6.85 | 631 | — |
| 27 | 6.28 | 403 | — |
| 28 | 6.35 | 409 | — |
| 29 | — | 593 | — |
| 30 | 6.29 | 551 | — |
| 31 | — | 495 | — |
| 32 | 6.42 | 422 | 1 |
| 33 | 6.56 | 519 | — |
| 34 | — | 237 | — |
| 35 | 6.88 | 599 | — |
| 36 | 7.13 | 869 | — |
| 37 | — | 293 | — |
| 38 | 8.26 | 1156 | — |
| 39 | 6.06 | 498 | 2 |
| 40 | 7.00 | 965 | 2 |
| 41 | 6.99 | 657 | — |
| 42 | 7.98 | 827 | — |
| 43 | 7.22 | 663 | — |
| 44 | 6.55 | 607 | — |
| 45 | 6.45 | 566 | — |
| 46 | 6.48 | 610 | — |
| 47 | — | 247 | — |
| 48 | 6.18 | 1467 | 2 |
| 49 | 7.58 | 1004 | — |
| 50 | 7.18 | 953 | — |
| 51 | 7.22 | 960 | — |
| 52 | 5.21 | 582 | — |
| 53 | 5.55 | 1615 | — |
| 54 | 6.19 | 1449 | — |
| 55 | 6.10 | 1158 | — |
| 56 | 6.63 | 1503 | — |
| 57 | 6.16 | 783 | — |
| 58 | 6.53 | 1292 | — |
| 59 | 5.79 | 938 | — |
| 60 | — | 495 | — |
| 61 | 6.01 | 1194 | — |
| 62 | 5.37 | 633 | — |
| 63 | 5.74 | 969 | — |
| 64 | — | 980 | — |
| 65 | 5.49 | 1357 | — |
| 66 | 5.92 | 1082 | — |
| 67 | 5.27 | 959 | — |
| 68 | 6.04 | 1178 | — |
| 69 | 6.02 | 645 | 2 |
| 70 | 7.09 | 1642 | — |
| 71 | 6.16 | 1287 | 2 |
| 72 | 5.70 | 2118 | — |
| 73 | 6.14 | 1082 | 2 |
| 74 | 5.70 | 1885 | — |
| 75 | 5.99 | 819 | 2 |
| 76 | 6.26 | 611 | 2 |
| 77 | 6.97 | 809 | — |
| 78 | 5.93 | 919 | 2 |
| 79 | 5.78 | 1007 | — |
| 80 | 6.18 | 902 | — |
| 81 | 6.53 | 384 | 2 |
| 82 | 6.49 | 459 | 1 |
| 83 | 6.84 | 584 | 2 |
| 84 | 6.99 | 443 | 2 |
| 85 | 6.15 | 320 | 0 |
| 86 | 6.12 | 479 | — |
| 87 | 6.09 | 646 | 2 |
| 88 | 6.25 | 736 | 2 |
| 89 | 6.20 | 528 | 2 |
| 90 | 6.31 | 491 | 2 |
| 91 | 6.39 | 445 | — |
| 92 | 6.18 | 523 | — |
| 93 | 6.32 | 477 | — |
| 94 | 6.32 | 420 | — |
| 95 | 5.68 | 299 | — |
| 96 | 6.17 | 420 | — |
| 97 | 5.52 | 424 | — |
| 98 | 5.39 | 1052 | — |
| 99 | 5.13 | 1485 | — |
| 100 | 5.74 | 1209 | — |
| 101 | 5.18 | 1821 | — |
| 102 | 6.46 | 982 | — |
| 103 | 5.89 | 1176 | — |
| 104 | 7.21 | 923 | — |

TABLE 9-continued

Potency (pEC$_{50}$) and % efficacy for a number of compounds.

| Co. Nr. | a7-PAM-G_[33]_pEC50 pEC50 | a7-PAM-G_[33]_Eff_Curve_FI % Efficacy | PAM_Type PAM type |
|---|---|---|---|
| 105 | 6.54 | 895 | — |
| 106 | 7.09 | 650 | — |
| 107 | 7.57 | 780 | — |
| 108 | 7.14 | 764 | — |
| 109 | 6.65 | 826 | — |
| 110 | 7.91 | 957 | — |
| 111 | — | 812 | — |
| 112 | — | 525 | — |
| 113 | 5.56 | 730 | — |
| 114 | — | 313 | — |
| 115 | 5.03 | 230 | — |
| 116 | — | 259 | — |
| 117 | — | 665 | — |
| 118 | 5.73 | 430 | 0 |
| 119 | 5.37 | 302 | — |
| 120 | — | 567 | — |
| 121 | 5.69 | 356 | — |
| 122 | 6.00 | 473 | — |
| 123 | 6.41 | 636 | — |
| 124 | — | 356 | — |
| 125 | 6.07 | 428 | — |
| 126 | 5.78 | 655 | — |
| 127 | 6.16 | 1761 | — |
| 128 | 7.29 | 2697 | — |
| 129 | 6.04 | 1031 | — |
| 130 | 6.51 | 2600 | — |
| 131 | — | 462 | — |
| 133 | 6.94 | 1097 | — |
| 134 | 5.62 | 464 | 0 |
| 135 | 6.27 | 2048 | — |
| 136 | 5.71 | 1715 | — |
| 138 | 5.33 | 837 | — |
| 139 | 6.21 | 699 | — |
| 140 | 5.92 | 451 | — |
| 141 | 6.16 | 764 | — |
| 142 | — | 669 | — |
| 143 | 6.05 | 2200 | — |
| 144 | 5.67 | 1702 | 2 |
| 145 | 6.83 | 2696 | — |
| 146 | 6.01 | 1227 | — |
| 147 | 6.04 | 1074 | — |
| 148 | 5.91 | 1417 | 0 |
| 149 | 5.79 | 1766 | — |
| 150 | 6.37 | 894 | — |
| 151 | 6.06 | 1083 | — |
| 152 | 5.16 | 2546 | — |
| 153 | 5.56 | 1243 | — |
| 154 | 6.06 | 791 | 1 |
| 155 | 7.12 | 1554 | — |
| 156 | 5.90 | 2327 | 0 |
| 157 | 6.65 | 1797 | 2 |
| 158 | 5.80 | 951 | — |
| 159 | 5.01 | 704 | — |
| 160 | 5.09 | 1324 | — |
| 161 | 5.29 | 509 | — |
| 162 | 6.09 | 842 | — |
| 163 | — | 142 | — |
| 164 | 6.78 | 1214 | — |
| 165 | 7.31 | 1598 | — |
| 166 | 6.28 | 1237 | 1 |
| 167 | 5.91 | 2062 | — |
| 168 | 7.16 | 924 | 1 |
| 169 | — | 671 | — |
| 170 | 5.51 | 499 | — |
| 171 | 5.79 | 669 | — |
| 172 | 5.58 | 292 | — |
| 173 | 6.11 | 425 | — |
| 174 | 6.27 | 956 | — |
| 175 | 6.28 | 1074 | 1 |
| 176 | — | 149 | — |
| 177 | — | 26 | — |
| 178 | 6.30 | 733 | 0 |
| 179 | 7.01 | 707 | 2 |
| 180 | 5.72 | 1017 | — |
| 181 | 5.72 | 991 | — |
| 182 | 5.84 | 702 | — |
| 183 | 5.56 | 1372 | — |
| 184 | 6.25 | 974 | — |
| 185 | 5.32 | 835 | — |
| 186 | 5.42 | 945 | — |
| 187 | 5.28 | 994 | — |
| 188 | 5.30 | 685 | — |
| 189 | 5.82 | 1086 | — |
| 190 | 7.15 | 1089 | 2 |
| 191 | 7.13 | 995 | 2 |
| 192 | 6.63 | 670 | 2 |
| 193 | 7.68 | 1178 | 4 |
| 194 | 7.26 | 1148 | 3 |
| 195 | 6.73 | 1643 | 0 |
| 196 | 7.25 | 819 | 2 |
| 197 | 6.44 | 1046 | 1 |
| 198 | 6.83 | 2165 | 1 |
| 199 | 6.66 | 1729 | — |
| 200 | 6.79 | 1098 | 1 |
| 201 | 6.61 | 930 | 1 |
| 202 | 7.67 | 735 | 2 |
| 203 | 8.14 | 1346 | — |
| 204 | 7.50 | 392 | — |
| 205 | 7.42 | 883 | — |
| 206 | 7.36 | 985 | — |
| 207 | 5.48 | 1085 | 1 |
| 208 | 6.22 | 898 | 2 |
| 209 | 5.50 | 705 | 0 |
| 210 | 5.40 | 632 | — |
| 211 | 5.31 | 246 | — |

The pEC$_{50}$ and % efficacy values are those from the Ca$^{2+}$ assay as described in D.1. The PAM type is obtained from the patch clamp current recording as described hereinbefore ("—" means no value).

Example D.3

Auditory Evoked Potential Test in DBA/2 Mice

The vehicle used was 20% hydroxypropyl-β-cyclodextrin (HP-β-CD) in water, acidified slightly with a few drops of tartaric acid. Both drug solution and vehicle were administered s.c. in a volume of 4 ml/kg.

Male DBA/2 mice (18-25 g) were obtained from Harlan SD (Indianapolis, Ind.) and group housed until the start of the experiment. Food (Purina Rodent Chow) and water were available ad libitum, and lighting was cycled at 12-hour intervals (lights on at 6:00 am).

The mice were anesthetized with chloral hydrate (400 mg/kg i.p.) and pyrazole (400 mg/kg i.p.) to retard the metabolism of the chloral hydrate. Anesthesia was supplemented periodically to maintain a surgical plane of anesthesia (80 mg/kg i.p. of chloral hydrate and pyrazole as needed). The animal was placed in a mouse adapter (Neuroprobe, Cabin John, Md.) for a Kopf stereotaxic instrument (Kopf Instruments, Tujunga, Calif.). Hollow ear bars, attached to miniature earphones that were connected to a sound amplifier (RadioShack), were placed adjacent to the externalization of the aural canal. Because the auditory evoked potentials are more consistent at a stable temperature of 36° C., body temperature was maintained at this level with a heating pad. The scalp was incised in order to clear the skin from the skull and a burr hole opened over the CA3 region of the hippocampus [−1.8 mm antero-posterior to bregma, +2.70 mm medio-lateral to the midline]. A teflon-coated, stainless steel wire microelectrode was inserted into the CA3 pyramidal cell layer of the hippocampus (1.65-1.70 mm below the dorsal brain surface). Final electrode location was identified by the presence of complex action potentials typical of hippocampal pyramidal neurons. Following the surgical procedure, a reference electrode was placed on the dura, anterior to bregma and contralateral to the recording electrode. The electrical activity was amplified 1000 times with a bandpass of 1 to 500 Hz, and led to an analog to digital converter (RC Electronics, Bakersfield, Calif.) for averaging by computer. Tones of 3000 Hz, 10 ms duration and 72 dB SPL (sound pressure level) were generated as a sine wave and presented in pairs, with a 500 ms intra-pair interval and 10 sec between pairs. Although DBA/2 mice suffer hearing loss as they age, these tones were within the audible range of the mice.

The ratio of the P20-N40 amplitude of response to the second (test) stimulus and the first (conditioning) stimulus provides a measure of sensory inhibition; the ratio of the test to the conditioning amplitude (TC ratio) is 0.5 or less for most rodent strains and normal humans. In the paired-click version of the AEP model, responses to 16 pairs of tones were averaged at 5-min intervals. Each average was filtered digitally with bandpass between 10 and 250 Hz. The maximum negativity between 20 and 60 ms after the two stimuli was selected as the N40 wave and measured relative to the preceding positivity, the P20 wave. The amplitude from the P20 to the N40 wave was determined for both the conditioning and the test response.

Five recordings (5-min period containing 16 pairs of stimuli each) were obtained before compound injection to establish baseline sensory processing performance. Each mouse was drug-naïve at the time of experimentation. Following compound administration, 5-min recordings were obtained for a total of 95 minutes.

Data Analysis

All data were analyzed by multivariate analysis of variance with repeated measures. When a significance level of $p<0.05$ versus baseline scores was maintained throughout the analyses, Fisher's LSD a posteriori analyses were performed to determine which time points were significant from the averaged baseline value.

The lowest active dose was:
Compound 18: 0.04 mg/kg s.c.
Compound 1: 0.63 mg/kg s.c.

The invention claimed is:
1. A compound having the formula (I)

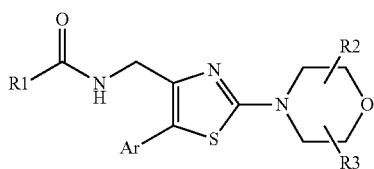

(I)

or a stereochemical isomer thereof, wherein
$R^1$ is $C_{1-6}$alkyl, $C_{1-6}$alkyl substituted with 1, 2 or 3 halogen substituents, $C_{1-6}$alkyl substituted with 1 cyano group, $C_{1-6}$alkyl substituted with 1 heteroaryl group, $C_{3-6}$cycloalkyl, $C_{3-6}$cycloalkyl substituted with 1, 2, 3, or 4 methyl groups, $C_{3-6}$cycloalkyl substituted with 1 hydroxy group, $(C_{3-6}$cycloalkyl)$C_{1-6}$alkyl, $(C_{1-6}$alkyloxy)$C_{1-6}$alkyl, (haloC$_{1-4}$alkyloxy)$C_{1-6}$alkyl, tetrahydrofuryl, aryl, heteroaryl, pyrrolidinyl, pyrrolidinyl substituted with 1 $C_{1-4}$-alkyl group, or tetrahydrofuryl substituted with 1, 2 or 3 substituents selected from methyl and oxo;
aryl is 2,2-difluoro-1,3-benzodioxolyl; phenyl; or phenyl substituted with 1, 2 or 3 substituents selected from halogen, trifluoromethyl, trifluoromethoxy, cyano, $C_{1-6}$alkyl, $C_{1-4}$alkyloxy, and aminosulfonyl;
heteroaryl is a mono- or bicyclic aromatic heterocyclic radical containing at least one heteroatom selected from N, O and S, optionally substituted with 1, 2 or where possible with 3 substituents selected from $C_{1-4}$alkyl, $C_{1-4}$alkyloxy, $C_{3-6}$cycloalkyl, and trifluoro-methyl;
$R^2$ and $R^3$ are independently H, $C_{1-4}$alkyl or trifluoromethyl;
or $R^2$ and $R^3$ are taken together to form 1,2-ethanediyl or 1,3-propanediyl;
Ar is

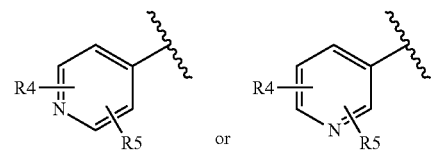

$R^4$ and $R^5$ are independently H, $C_{1-4}$alkyl, trifluoromethyl, $C_{3-6}$cycloalkyl or $C_{1-4}$alkyloxy;
or an acid addition salt thereof.
2. The compound according to claim 1 wherein
$R^1$ is $C_{1-6}$alkyl, $C_{1-4}$alkyl substituted with 3 fluoro substituents, methyl substituted with 1 cyano group, methyl substituted with 3,5-dimethyl-4-ixoxazolyl, methyl substituted with 3-methyl-5-isoxazolyl, $C_{3-6}$cycloalkyl, cyclopropyl substituted with 1, 2, 3, or 4 methyl groups, cyclopropyl substituted with 1 hydroxy group, $(C_{3-6}$cycloalkyl)$C_{1-2}$alkyl, methoxymethyl, methoxyethyl, (2,2,2-trifluoroethoxy)methyl, tetrahydrofuryl, aryl, heteroaryl, pyrrolidinyl substituted with 1 methyl group, or tetrahy-drofuryl substituted with 3 substituents selected from methyl and oxo;
aryl is 2,2-difluoro-1,3-benzodioxol-5-yl; 2,2-difluoro-1, 3-benzodioxol-4-yl; phenyl; or phenyl substituted with 1, 2 or 3 substituents selected from fluoro, chloro, trifluoro-methyl, trifluoromethoxy, cyano, methyl, methoxy, and aminosulfonyl;
heteroaryl is furanyl, oxazolyl, isoxazolyl, oxadiazolyl, pyrrolyl, pyrazolyl, imidazolyl, pyridinyl, pyridiminyl, pyrazinyl, pyridazinyl, thienyl, 1,2,3-thiadiazolyl, thiazolyl or benzisoxazolyl, each unsubstituted or substituted with 1, 2 or where possible 3 substituents selected from methyl, ethyl, propyl, isopropyl, butyl, isobutyl, tert.butyl, cyclopropyl, methoxy or trifluoromethyl.
3. The compound according to claim 1 wherein $R^2$ is hydrogen or methyl.
4. The compound according to claim 1 wherein $R^3$ is methyl.
5. The compound according to claim 1 wherein $R^4$ is H, methyl, trifluoromethyl, cyclopropyl or methoxy.
6. The compound according to claim 1 wherein $R^5$ is hydrogen or methyl.
7. The compound according to claim 1 wherein
$R^1$ is methyl, ethyl, n-propyl, isopropyl, n-butyl, isobutyl, tert.-butyl, cyclopropyl, 1-methylcyclopropyl, 2,2,3,3-tetramethylpropyl, cyclobutyl, cyclopentyl, (cyclopropyl)ethyl, (cyclopropyl)methyl, (cyclobutyl)methyl, 3 methyl-isoxazol-5-yl, 3-methyl-isoxazol-4-yl, 5-methyl-isoxazol-3-yl, 2-methyl-5-trifluoromethyl-oxazol-4-yl, or 2-methyl-oxazol-4-yl.

8. The compound according to claim 1 wherein $R^2$ and $R^3$ are methyl and have the cis-configuration.

9. The compound according to claim 1 wherein $R^5$ is methyl.

10. The compound according to claim 1 wherein the compound is

N-[[2-[(2R,6S)-2,6-dimethyl-4-morpholinyl]-5-(2,6-dimethyl-4-pyridinyl)-4-thiazolyl]methyl]-cyclopropaneacetamide;

N-[[2-[(2R,6S)-2,6-dimethyl-4-morpholinyl]-5-(2,6-dimethyl-4-pyridinyl)-4-thiazolyl]methyl]-3-methyl-4-isoxazolecarboxamide;

N-[[2-[(2R,6S)-2,6-dimethyl-4-morpholinyl]-5-(2,6-dimethyl-4-pyridinyl)-4-thiazolyl]methyl]-3-methyl-5-isoxazolecarboxamide; and N-[[2-[(2R,6S)-2,6-dimethyl-4-morpholinyl]-5-(2,6-dimethyl-4-pyridinyl)-4-thiazolyl]methyl]-acetamide.

11. A pharmaceutical composition comprising as active ingredient a therapeutically effective amount of a compound as defined in claim 1 and an excipient.

12. A pharmaceutical composition comprising (a) a therapeutically effective amount of a compound of formula (I) as defined in claim 1, and (b) a therapeutically effective amount of a α7 nicotinic receptor agonist selected from the group consisting of 1,4-Diazabicyclo[3.2.2]nonane-4-carboxylic acid, 4-bromophenyl ester, monohydrochloride (SSR180711A);

(−)-spiro[1-azabicyclo[2.2.2]octane-3,5′-oxazolidine]-2′-one;

(+)—N-(1-azabicyclo[2.2.2]oct-3-yl)benzo[b]furan-2-carboxamide;

3-[(2,4-Dimethoxy)Benzylidene]-Anabaseine Dihydrochloride (GTS-21);

[N-[(3R)-1-Azabicyclo[2.2.2]oct-3-yl]-4-chlorobenzamide Hydrochloride] PNU-282987; nicotine; varenicline; A-582941; AR-R17779; TC-1698; PHA-709829; tropisetron; WAY-317538; MEM3454; EVP-6124; TC-5619; MEM-63908; and AZD-0328, as a combined preparation for simultaneous, separate or sequential use.

13. A method of treatment comprising administering a therapeutically effective amount of compound as defined in claim 1 to a patient in need of treatment for a disorder selected from the group consisting of Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma, jetlag, nicotine addiction, pain; endotoxaemia, endotoxic shock, sepsis, rheumatoid arthritis, asthma, multiple sclerosis, psoriasis, urticaria, inflammatory bowel disease, inflammatory bile disease, Crohn's disease, ulcerative colitis, post-operative ileus, pancreatitis, post-operative heart failure, post-operative acute lung injury, post-operative allograft rejection, or mild cognitive impairment.

14. A process of preparing a pharmaceutical composition comprising the step of intimately mixing a pharmaceutically acceptable carrier with a therapeutically effective amount of a compound as defined in claim 1.

\* \* \* \* \*